(12) United States Patent
Ricci et al.

(10) Patent No.: US 9,238,670 B2
(45) Date of Patent: Jan. 19, 2016

(54) AMINOGLYCOSIDE ANTIBIOTICS WITH REDUCED OTOTOXICITY

(71) Applicant: The Board of Trustees of the Leland Stanford Junior University, Palo Alto, CA (US)

(72) Inventors: Anthony J. Ricci, Stanford, CA (US); Robert J. Greenhouse, Newark, CA (US); Alan G. Cheng, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 21 days.

(21) Appl. No.: 14/212,964

(22) Filed: Mar. 14, 2014

(65) Prior Publication Data

US 2014/0274932 A1    Sep. 18, 2014

Related U.S. Application Data

(60) Provisional application No. 61/792,256, filed on Mar. 15, 2013.

(51) Int. Cl.
*A61K 31/70* (2006.01)
*C07H 15/236* (2006.01)
*C07D 407/12* (2006.01)

(52) U.S. Cl.
CPC ............ *C07H 15/236* (2013.01); *C07D 407/12* (2013.01)

(58) Field of Classification Search
CPC ......................... C07H 15/236; C07D 407/12
See application file for complete search history.

(56) References Cited

U.S. PATENT DOCUMENTS 4,199,572 A * 4/1980 Schroder et al. ................ 514/41

FOREIGN PATENT DOCUMENTS

DE         2408227 A1    8/1974

* cited by examiner

*Primary Examiner* — Elli Peselev
(74) *Attorney, Agent, or Firm* — Mintz Levin Cohn Ferris Glovsky and Popeo, P.C.; Shovon Ashraf, J.D.

(57) ABSTRACT

This disclosure relates generally to aminoglycoside derivatives of Formula (I) as described herein. The present disclosure also relates to pharmaceutical compositions containing these compounds and methods of treating bacterial infections by administering these compounds and pharmaceutical compositions to subjects in need thereof.

19 Claims, 3 Drawing Sheets

AMINOGLYCOSIDE ANTIBIOTICS WITH REDUCED OTOTOXICITY

RELATED APPLICATIONS

This application claims priority to, and the benefit of, U.S. provisional application No. 61/792,256, filed Mar. 15, 2013, the entire content of which is incorporated herein by reference in its entirety.

GOVERNMENT SUPPORT

This invention was made with U.S. Government support under NIH/NIDCD grant R21 DC012183. The Government has certain rights in the invention.

BACKGROUND

Aminoglycoside antibiotics are a well-known class of antibiotics with an established record of both efficacy and safety. These compounds are used largely for gram-negative bacteria but are also broad spectrum antibiotics with little resistance developed at this point. Patients treated with aminoglycoside antibiotics include immune compromised patients, such as newborns and their mothers, and cystic fibrosis patients. Aminoglycosides are also used as preservatives.

The primary use-limiting adverse reactions associated with the class are ototoxicity and nephrotoxicity. See, e.g., Rizzi and Hirose, *Curr Opin Otolaryngol Head Neck Surg* 15:352-357, 2007. Despite their ototoxic and nephrotoxic effects, aminoglycoside antibiotics remain one of the most widely used antibiotics worldwide.

Given the importance of aminoglycosides in treating multiple infections, new aminoglycosides having reduced ototoxicity and/or nephrotoxicity are needed. The present invention addresses these needs.

SUMMARY OF THE DISCLOSURE

The present disclosure provides, in part, novel aminoglycoside derivatives with reduced ototoxicity. In one aspect, the invention relates to a compound of Formula (I) or a pharmaceutically acceptable salt thereof:

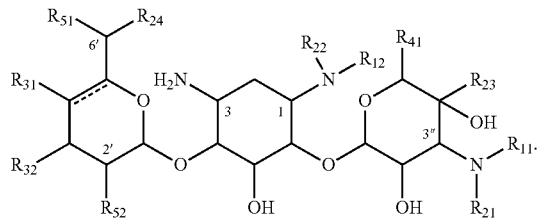

(I)

In this formula, the ≡ bond is a single bond or double bond;

each of $R_{11}$ and $R_{12}$ independently is H, $C(O)R_a$, $C(O)OR_a$, $C(O)NHR_a$, $C(O)NR_aR_b$, or $S(O)_nR_a$, in which n is 1, or 2, and each of $R_a$ and $R_b$, independently is $C_1$-$C_{20}$ alkyl, $C_2$-$C_{20}$ alkenyl, $C_2$-$C_{20}$ alkynyl, $C_3$-$C_8$ cycloalkyl, $C_6$-$C_{10}$ aryl, 4 to 12-membered heterocycloalkyl, or 5 to 14-membered heteroaryl; or $R_a$ and $R_b$, together with the N atom to which they are attached, form a 4 to 12-membered heterocycloalkyl ring having 0 or 1 additional heteroatom; and each of $R_a$, $R_b$, and the 4 to 12-membered heterocycloalkyl ring formed by $R_a$ and $R_b$, is optionally substituted;

each of $R_{21}$, $R_{22}$, $R_{23}$, and $R_{24}$, independently, is H or optionally substituted $C_1$-$C_6$ alkyl;

each of $R_{31}$ and $R_{32}$, independently, is H or OH;

$R_{41}$ is H or $CH_2OH$; and each of $R_{51}$ and $R_{52}$, independently, is OH, $NH_2$, unsubstituted mono-$C_1$-$C_6$ alkylamino, or unsubstituted di-$C_1$-$C_6$ alkylamino, provided that at least one of $R_{11}$ and $R_{12}$ is not H; further when $R_{12}$ is $C(O)R_a$ or $S(O)_2R_a$, then $R_a$ is not alkyl substituted with $NH_2$.

In another aspect, the invention relates to a compound of Formula (I) above or a pharmaceutically acceptable salt thereof, wherein:

the ≡ bond is a single bond or double bond;

each of $R_{11}$ and $R_{12}$ independently is H, $C(O)R_a$, $C(O)OR_a$, $C(O)NHR_a$, $C(O)NR_aR_b$, or $S(O)_nR_a$, in which n is 1, or 2, and each of $R_a$ and $R_b$, independently is $C_1$-$C_{20}$ alkyl, $C_2$-$C_{20}$ alkenyl, $C_2$-$C_{20}$ alkynyl, $C_3$-$C_8$ cycloalkyl, $C_6$-$C_{10}$ aryl, 4 to 12-membered heterocycloalkyl, or 5 to 14-membered heteroaryl; or $R_a$ and $R_b$, together with the N atom to which they are attached, form a 4 to 12-membered heterocycloalkyl ring having 0 or 1 additional heteroatom; and each of $R_a$, $R_b$, and the 4 to 12-membered heterocycloalkyl ring formed by $R_a$ and $R_b$, is optionally substituted;

each of $R_{21}$, $R_{22}$, $R_{23}$, and $R_{24}$, independently, is H or optionally substituted $C_1$-$C_6$ alkyl;

each of $R_{31}$ and $R_{32}$, independently, is H or OH;

$R_{41}$ is H or $CH_2OH$; and each of $R_{51}$ and $R_{52}$, independently, is OH, $NH_2$, unsubstituted mono-$C_1$-$C_6$ alkylamino, or unsubstituted di-$C_1$-$C_6$ alkylamino, provided that at least one of $R_{11}$ and $R_{12}$ is not H; further when $R_{12}$ is $C(O)R_a$ or $S(O)_2R_a$ and $R_a$ is alkyl, then $R_a$ is unsubstituted alkyl or alkyl substituted with one or more -Q-T, wherein Q is a bond or $C_1$-$C_3$ alkyl linker each optionally substituted with halo, cyano, hydroxyl or $C_1$-$C_6$ alkoxy, and T is H, halo, cyano, $-OR_c$, $-C(O)R_c$, $-C(O)OR_c$, $-C(O)NR_cR_d$, $-NR_dC(O)R_c$, $-NR_dC(O)OR_c$, $-S(O)_2R_c$, $-S(O)_2NR_cR_d$, $R_{S1}$, $-NHR_{S1}$, or $-N(R_{S1})_2$, in which each of $R_c$ and $R_d$, independently is H or $R_{S2}$, each of $R_{S1}$ and $R_{S2}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl; or $R_c$ and $R_d$, together with the N atom to which they are attached, form a 4 to 12-membered heterocycloalkyl ring having 0 or 1 additional heteroatom or 5 to 14-membered heteroaryl.

In another aspect, the invention also provides a compound of Formula (III) or a pharmaceutically acceptable salt thereof:

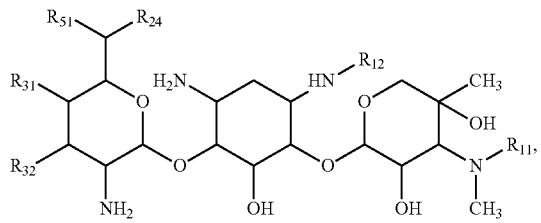

(III)

wherein each of $R_{11}$ and $R_{12}$ independently is H, $C(O)R_a$, $C(O)OR_a$, $C(O)NHR_a$, $C(O)NR_aR_b$, or $S(O)_nR_a$, in which n is 1, or 2, and each of $R_a$ and $R_b$, independently is $C_1$-$C_{20}$ alkyl, $C_2$-$C_{20}$ alkenyl, $C_2$-$C_{20}$ alkynyl, $C_3$-$C_8$ cycloalkyl, $C_6$-$C_{10}$ aryl, 4 to 12-membered heterocycloalkyl, or 5 to 14-membered heteroaryl; or $R_a$ and $R_b$, together with the N atom to which they are attached, form a 4 to 12-membered heterocycloalkyl ring having 0 or 1 additional heteroatom; and each of $R_a$, $R_b$, and the 4 to 12-membered heterocycloalkyl ring formed by $R_a$ and $R_b$, is optionally substituted; provided that at least one of $R_{11}$ and $R_{12}$ is not H;

$R_{24}$ is H or methyl;

$R_{31}$ and $R_{32}$ are the same and are H or OH; and $R_{51}$ is OH, $NH_2$, or $NHCH_3$.

The present invention also provides pharmaceutical compositions comprising one or more pharmaceutically acceptable carriers and one or more compounds selected from those of any of the Formulae described herein.

Another aspect of this invention relates to a method of treating or preventing a bacterial infection, such as an infection caused gram-negative bacteria, gram-positive bacteria, and/or mycobacteria. The method includes administering to a subject in need thereof a therapeutically effective amount of one or more compounds selected from those of any of the Formulae described herein. For example, the subject in need thereof is immunodeficient (e.g., immunosuppressed). For example, the subject in need thereof has intact immune responses. For example, the subject in need thereof is an infant, a pediatric patient, or a pregnant woman.

Unless otherwise stated, any description of a method of treatment includes uses of the compounds to provide such treatment or prophylaxis as is described in the specification, as well as uses of the compounds to prepare a medicament to treat or prevent such condition. The treatment includes treatment of human or non-human animals including rodents and other disease models.

Further, the invention provides a method of preparing one or more compounds selected from those of any of the Formulae described herein.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting. In the case of conflict between the chemical structures and names of the compounds disclosed herein, the chemical structures will control.

Other features and advantages of the invention will be apparent from the following brief description of the drawings, detailed description, and claims.

DETAILED DESCRIPTION OF THE INVENTION

Figure 1:
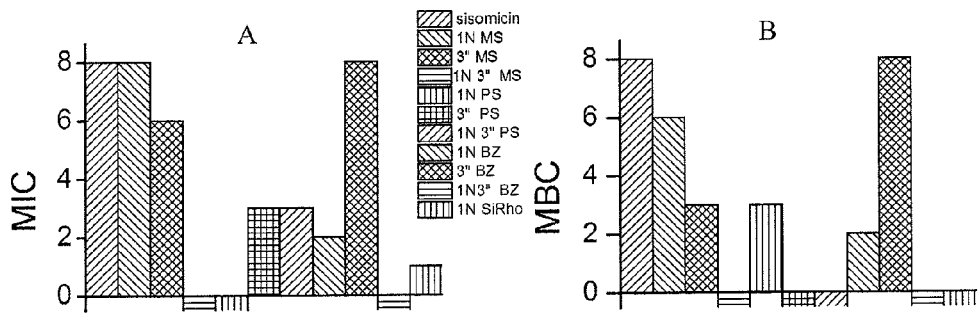
FIGS. 1A and 1B are bar graphs showing antimicrobial activities of a variety of sisomicin derivatives (MS=methyl sulfonyl, PS=phenyl sulfonyl, BZ=benzoyl, SiRho=rhodamine; and 1N and 3" indicate substituents' position on sisomicin). The negative values reflect an arbitrary value indicating no detectable level of activity.

Previous attempts to ameliorate the toxic side effects of aminoglycoside antibiotics have met with mixed results. For example, modulating dosage plans failed to reduce toxic side effects in certain patients, as susceptibility levels vary among patients. Similarly, treatments to increase free radical scavengers or to inhibit apoptotic pathways have all had mixed results (see, e.g., Rybak and Ramkumar, *Kidney Int* 72:931-935, 2007). A confounding problem has been that the aminoglycoside compounds are not metabolized by the sensory cells that they enter and so can result in long term toxic side effects.

In one aspect, the present invention is based in part on a recent unexpected discovery that conventional aminoglycosides (such as gentamicin) enter hair cells at high levels by passing through a specific ion channel, i.e., the mechanically gated channel located in the sensory hair bundle that is critical for hearing process (see, e.g., Alharazneh et al., *PLoS One* 6:e22347, 2011; Huth et al., *International Journal of Otolaryngology*, 1-19, 2011; Waguespack and Ricci, *J Physiol* 567.2 (2005) 359-360; Farris et al., *J Physiol* 558:769-792, 2004; Pan et al., *J Neurophysiol* 107:2408-2420, 2012; and Vu et al., *PLoS One* 8(1): e54794, 2013). A similar mechanism for kidney cells is postulated. Accordingly, the present invention in part provides a method for designing novel aminoglycoside compounds that cannot enter the sensory cells and/or have enhanced ability to leave the sensory cells so that these modified aminoglycoside compounds cannot accumulate within the sensory cells and thus cannot cause toxicity.

In one embodiment, molecular sites of the parent aminoglycoside compound that are of lesser importance to the antimicrobial activity of the compound are selected to be modified, based on crystal structures of the parent aminoglycoside compound (see, e.g., Yoshizawa et al., *EMBO J* 17:6437-6448, 1998; Recht et al., *EMBO J* 18:3133-3138, 1999; Lynch and Puglisi, *J Mol Biol* 306:1037-1058, 2001; Sutcliffe, *Curr Opin Microbiol* 8:534-542, 2005; and Borovinskaya et al., *Nat Struct Mol Biol* 14:727-732, 2007). In one embodiment, the modification sites and/or modifying substituents to those sites are selected and optimized based on the degree of separation between $EC_{50}$ for antimicrobial action and $LD_{50}$ in terms of renal or inner ear damage. In embodiments, aminoglycoside compounds of the invention, which have greater separation between the $EC_{50}$ and $LD_{50}$ values, are preferred.

For example, the parent aminoglycoside compounds to be modified are selected from sisomicin, gentamicin, gentamicin C1a, gentamicin C2, gentamicin C2a, gentamicin C2b, gentamicin X, kanamycin A, kanamycin B, kanamycin C, tobramycin, verdamicin, dibekasin, netilmicin, and 5-epinetilmicin.

In one embodiment, the selected sites are the amino (including mono-alkyl amino) groups of the parent aminoglycosides. In one embodiment, only one or two of the amino groups are modified. In one embodiment, the selected sites include 1N-position and 3″N-position of See, also, —$NR_{12}R_{22}$ and —$NR_{11}R_{21}$ groups in Formula (I) described herein. In certain embodiments, aminoglycoside compounds having modification in only one or two of the amino groups of the parent aminoglycosides are less ototoxic than the parent aminoglycosides and less toxic than those compounds with modifications in more than three (e.g., four, five, or all) of the amino groups of the parent aminoglycosides.

In one embodiment, these selected sites are modified to reduce net charge or to reduce basicity of the parent aminoglycoside compound so as to reduce the driving force for it to enter the cells. In one embodiment, these selected sites are modified to enhance steric hindrance by e.g., including one or more bulky moieties to one or more of these sites, so that the compound as modified cannot permeate the ion channel pore. In one embodiment, these selected sites are modified to both reduce net charge and to enhance steric hindrance.

In one embodiment, only one of the 1N-position and 3″N-position of the parent aminoglycoside compounds is modified and the other is unchanged. In one embodiment, both the 1N-position and the 3″N— position are modified, and one position is modified to a greater level than the other position in terms of steric hindrance and/or net charge reduction. In certain embodiments, aminoglycoside compounds with great modification at only one position of the 1N- and 3″N-positions are less ototoxic than the parent aminoglycosides, and are also less ototoxic than those compounds with great modifications at both the 1N- and 3″N-positions.

The present invention also provides novel aminoglycoside antibiotics, synthetic methods for making these compounds, pharmaceutical compositions containing them and various uses of the compounds.

Aminoglycoside Derivatives

In one aspect, the present invention provides the compounds of Formula (I):

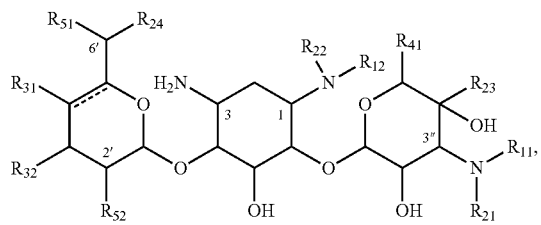

(I)

wherein
the ═══ bond is a single bond or double bond;
each of $R_{11}$ and $R_{12}$ independently is H, $C(O)R_a$, $C(O)OR_a$, $C(O)NHR_a$, $C(O)NR_aR_b$, or $S(O)_nR_a$, in which n is 1, or 2, and each of $R_a$ and $R_b$, independently is $C_1$-$C_{20}$ alkyl, $C_2$-$C_{20}$ alkenyl, $C_2$-$C_{20}$ alkynyl, $C_3$-$C_8$ cycloalkyl, $C_6$-$C_{10}$ aryl, 4 to 12-membered heterocycloalkyl, or 5 to 14-membered heteroaryl; or $R_a$ and $R_b$, together with the N atom to which they are attached, form a 4 to 12-membered heterocycloalkyl ring having 0 or 1 additional heteroatom; and each of $R_a$, $R_b$, and the 4 to 12-membered heterocycloalkyl ring formed by $R_a$ and $R_b$, is optionally substituted;

each of $R_{21}$, $R_{22}$, $R_{23}$, and $R_{24}$, independently, is H or optionally substituted $C_1$-$C_6$ alkyl;
each of $R_{31}$ and $R_{32}$, independently, is H or OH;
$R_{41}$ is H or $CH_2OH$; and
each of $R_{51}$ and $R_{52}$, independently, is OH, $NH_2$, unsubstituted mono-$C_1$-$C_6$ alkylamino, or unsubstituted di-$C_1$-$C_6$ alkylamino, provided that at least one of $R_{11}$ and $R_{12}$ is not H; further when $R_{12}$ is $C(O)R_a$ or $S(O)_2R_a$, then $R_a$ is not alkyl substituted with $NH_2$.

In another aspect, the invention relates to a compound of Formula (I) above or a pharmaceutically acceptable salt thereof, wherein:
the ═══ bond is a single bond or double bond;
each of $R_{11}$ and $R_{12}$ independently is H, $C(O)R_a$, $C(O)OR_a$, $C(O)NHR_a$, $C(O)NR_aR_b$, or $S(O)_nR_a$, in which n is 1, or 2, and each of $R_a$ and $R_b$, independently is $C_1$-$C_{20}$ alkyl, $C_2$-$C_{20}$ alkenyl, $C_2$-$C_{20}$ alkynyl, $C_3$-$C_8$ cycloalkyl, $C_6$-$C_{10}$ aryl, 4 to 12-membered heterocycloalkyl, or 5 to 14-membered heteroaryl; or $R_a$ and $R_b$, together with the N atom to which they are attached, form a 4 to 12-membered heterocycloalkyl ring having 0 or 1 additional heteroatom; and each of $R_a$, $R_b$, and the 4 to 12-membered heterocycloalkyl ring formed by $R_a$ and $R_b$, is optionally substituted;

each of $R_{21}$, $R_{22}$, $R_{23}$, and $R_{24}$, independently, is H or optionally substituted $C_1$-$C_6$ alkyl;
each of $R_{31}$ and $R_{32}$, independently, is H or OH;
$R_{41}$ is H or $CH_2OH$; and
each of $R_{51}$ and $R_{52}$, independently, is OH, $NH_2$, unsubstituted mono-$C_1$-$C_6$ alkylamino, or unsubstituted di-$C_1$-$C_6$ alkylamino, provided that at least one of $R_{11}$ and $R_{12}$ is not H; further when $R_{12}$ is $C(O)R_a$ or $S(O)_2R_a$ and $R_a$ is alkyl, then $R_a$ is unsubstituted alkyl or alkyl substituted with one or more -Q-T, wherein Q is a bond or $C_1$-$C_3$ alkyl linker each optionally substituted with halo, cyano, hydroxyl or $C_1$-$C_6$ alkoxy, and T is H, halo, cyano, —$OR_c$, —$C(O)R_c$, —$C(O)OR_c$, —$C(O)NR_cR_d$, —$NR_aC(O)R_c$, —$NR_aC(O)OR_e$, —$S(O)_2R_c$, —$S(O)_2NR_cR_d$, $R_{S1}$, —$NHR_{S1}$, or —$N(R_{S1})_2$, in which each of $R_c$ and $R_d$, independently is H or $R_{S2}$, each of $R_{S1}$ and $R_{S2}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl; or $R_c$ and $R_d$, together with the N atom to which they are attached, form a 4 to 12-membered heterocycloalkyl ring having 0 or 1 additional heteroatom or 5 to 14-membered heteroaryl.

A subset of compounds of Formula (I) includes those of Formula (II) or pharmaceutically acceptable salts thereof:

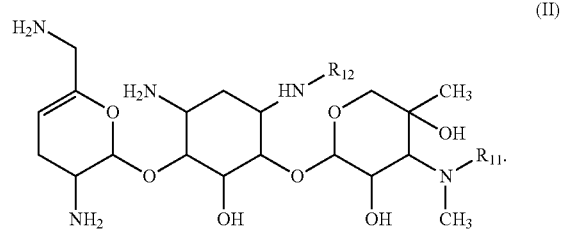

(II)

A subset of compounds of Formula (II) includes those of Formula (IIA) or pharmaceutically acceptable salts thereof:

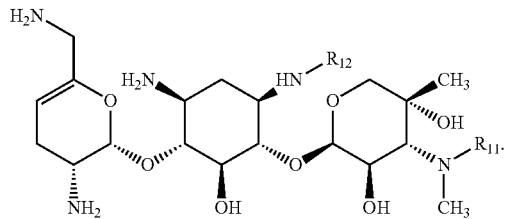
(IIA)

Another subset of compounds of Formula (II) includes those of Formula (IIB) or pharmaceutically acceptable salts thereof:

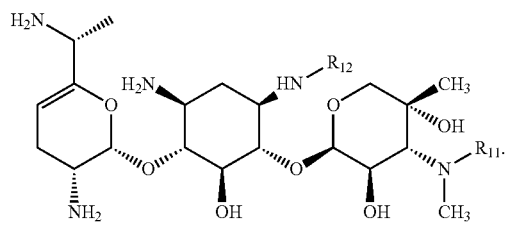
(IIB)

Yet another subset of compounds of Formula (II) includes those of Formula (IIC) or pharmaceutically acceptable salts thereof:

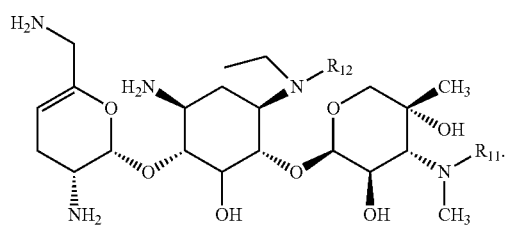
(IIC)

A subset of compounds of Formula (I) above includes those of Formula (IV) or pharmaceutically acceptable salts thereof:

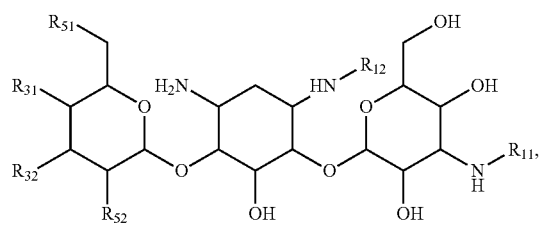
(IV)

wherein each of $R_{51}$ and $R_{52}$, independently, is OH or $NH_2$.

Subsets of compounds of Formula (IV) includes those of any of Formulae (IVA)-(IVE) or pharmaceutically acceptable salts thereof:

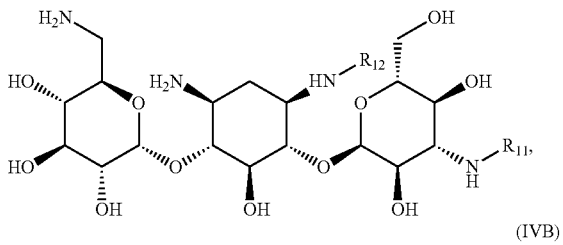
(IVA)

(IVB)

(IVC)

(IVD)

(IVE)

, or

In another aspect, the invention provides a compound of Formula (III) or a pharmaceutically acceptable salt thereof:

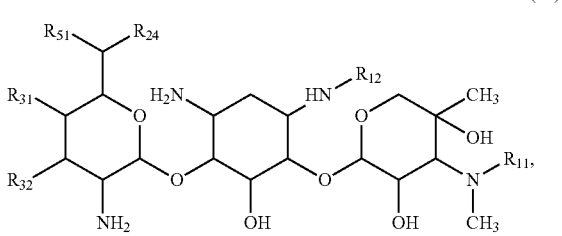
(III)

wherein
each of $R_{11}$ and $R_{12}$ independently is H, C(O)$R_a$, C(O)O$R_a$, C(O)NH$R_a$, C(O)N$R_a R_b$, or S(O)$_n R_a$, in which n is 1, or 2, and each of $R_a$ and $R_b$, independently is $C_1$-$C_{20}$ alkyl, $C_2$-$C_{20}$ alkenyl, $C_2$-$C_{20}$ alkynyl, $C_3$-$C_8$ cycloalkyl, $C_6$-$C_{10}$ aryl, 4 to 12-membered heterocycloalkyl, or 5 to 14-membered heteroaryl; or $R_a$ and $R_b$, together with the N atom to which they are attached, form a 4 to 12-membered heterocycloalkyl ring having 0 or 1 additional heteroatom; and each of $R_a$, $R_b$, and the 4 to 12-membered heterocycloalkyl ring formed by $R_a$ and $R_b$, is optionally substituted; provided that one of $R_{11}$ and $R_{12}$ is not H;

$R_{24}$ is H or methyl;

$R_{31}$ and $R_{32}$ are the same and are H or OH; and $R_{51}$ is OH, NH$_2$, or NHCH$_3$.

Subsets of compounds of Formula (III) include compounds of any of Formulae (IIIA)-(IIIF) or pharmaceutically acceptable salts thereof:

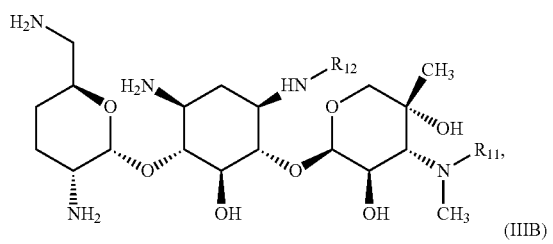
(IIIA)

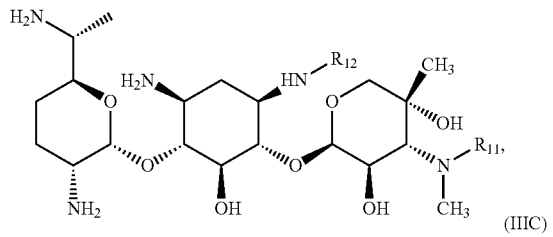
(IIIB)

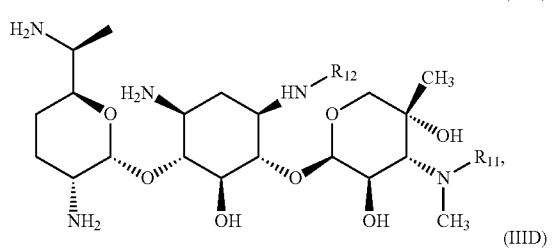
(IIIC)

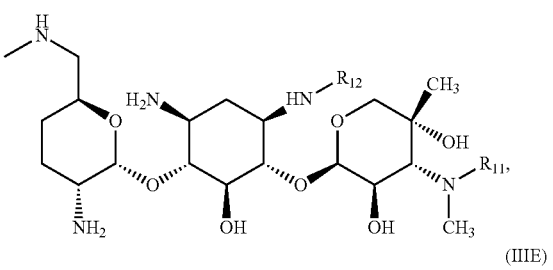
(IIID)

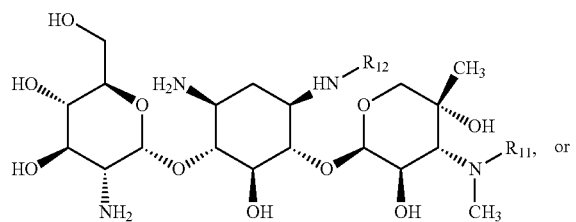
(IIIE)

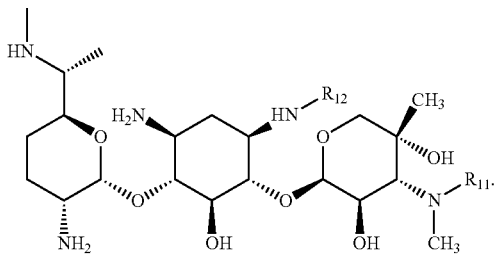
(IIIF)

The compound of any of the Formulae above can have one or more of the following features, when applicable.

For example, $R_{11}$ is H and $R_{12}$ is not H.

For example, neither of $R_{11}$ and $R_{12}$ is H.

For example, $R_{12}$ is H and $R_{11}$ is not H.

For example, $R_{12}$ is C(O)$R_a$ or S(O)$_2 R_a$.

For example, $R_{12}$ is C(O)$R_a$ or S(O)$_2 R_a$, and $R_a$ is not alkyl substituted with NH$_2$.

For example, $R_{11}$ is C(O)$R_a$ or S(O)$_2 R_a$.

For example, $R_{11}$ is C(O)$R_a$ or S(O)$_2 R_a$, and $R_a$ is not alkyl substituted with NH$_2$.

For example, each of $R_{11}$ and $R_{12}$ independently is C(O)$R_a$ or S(O)$_2 R_a$.

For example, one of $R_{11}$ and $R_{12}$ is C(O)$R_a$ or S(O)$_2 R_a$ and the other is H.

For example, each of $R_a$ independently is unsubstituted alkyl, alkyl substituted by one or more halo or $C_3$-$C_8$ cycloalkyl, optionally substituted phenyl, optionally substituted $C_{3-8}$ cycloalkyl, optionally substituted 4 to 12-membered heterocycloalkyl, or optionally substituted 5 to 14-membered heteroaryl.

For example, each of $R_a$ independently is methyl, phenyl, 2-nitrophenyl, n-propyl, i-propyl, i-butyl, t-butyl, cyclopropyl, —CH$_2$-cyclopropyl, cyclopentyl, —(CH$_2$)$_9$CH$_3$, —(CH$_2$)$_6$CH$_3$, CF$_3$, —CH$_2$CF$_3$, —CF$_2$CF$_3$, CCl$_3$, 3-pyridyl, or 4-pyridyl.

For example, $R_{12}$ is S(O)$_2 R_a$, and $R_a$ is unsubstituted alkyl (e.g., methyl, ethyl, n-propyl, i-propyl, i-butyl, t-butyl, —(CH$_2$)$_9$CH$_3$, or —(CH$_2$)$_6$CH$_3$).

For example, $R_{12}$ is S(O)$_2 R_a$, and $R_a$ is alkyl substituted by one or more halo or $C_3$-$C_8$ cycloalkyl, e.g., —CH$_2$-cyclopropyl, CF$_3$, —CH$_2$CF$_3$, —CF$_2$CF$_3$, or CCl$_3$.

For example, $R_{12}$ is S(O)$_2 R_a$, and $R_a$ is optionally substituted phenyl (e.g., phenyl, 2-nitrophenyl).

For example, $R_{12}$ is S(O)$_2 R_a$, and $R_a$ is optionally substituted $C_{3-8}$ cycloalkyl (e.g., cyclopropyl or cyclopentyl).

For example, $R_{12}$ is S(O)$_2 R_a$, and $R_a$ is optionally substituted 4 to 12-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like).

For example, $R_{12}$ is S(O)$_2 R_a$, and $R_a$ is optionally substituted 5 to 14-membered heteroaryl (e.g., pyrrolyl, furyl, thiophenyl, thiazolyl, isothiazolyl, imidazolyl, triazolyl, tetrazolyl, pyrazolyl, oxazolyl, isoxazolyl, pyridyl, pyrazinyl, pyridazinyl, or pyrimidyl).

For example, $R_{12}$ is S(O)$_2 R_a$, and $R_a$ is methyl, phenyl, 2-nitrophenyl, n-propyl, i-propyl, i-butyl, t-butyl, cyclopropyl, —CH$_2$-cyclopropyl, cyclopentyl, —(CH$_2$)$_9$CH$_3$, —(CH$_2$)$_6$CH$_3$, CF$_3$, —CH$_2$CF$_3$, —CF$_2$CF$_3$, CCl$_3$, 3-pyridyl, or 4-pyridyl.

For example, $R_{12}$ is $C(O)_2R_a$, and $R_a$ is unsubstituted alkyl (e.g., methyl, ethyl, n-propyl, i-propyl, i-butyl, t-butyl, —(CH$_2$)$_9$CH$_3$, or —(CH$_2$)$_6$CH$_3$).

For example, $R_{12}$ is $C(O)_2R_a$, and $R_a$ is alkyl substituted by one or more halo or $C_3$-$C_8$ cycloalkyl, e.g., —CH$_2$-cyclopropyl, CF$_3$, —CH$_2$CF$_3$, —CF$_2$CF$_3$, or CCl$_3$.

For example, $R_{12}$ is $C(O)_2R_a$, and $R_a$ is optionally substituted phenyl (e.g., phenyl, 2-nitrophenyl).

For example, $R_{12}$ is $C(O)_2R_a$, and $R_a$ is optionally substituted $C_{3-8}$ cycloalkyl (e.g., cyclopropyl or cyclopentyl).

For example, $R_{12}$ is $C(O)_2R_a$, and $R_a$ is optionally substituted 4 to 12-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like).

For example, $R_{12}$ is $C(O)_2R_a$, and $R_a$ is optionally substituted 5 to 14-membered heteroaryl (e.g., pyrrolyl, furyl, thiophenyl, thiazolyl, isothiazolyl, imidazolyl, triazolyl, tetrazolyl, pyrazolyl, oxazolyl, isoxazolyl, pyridyl, pyrazinyl, pyridazinyl, or pyrimidyl).

For example, $R_{12}$ is $C(O)_2R_a$, and $R_a$ is methyl, phenyl, 2-nitrophenyl, n-propyl, i-propyl, i-butyl, t-butyl, cyclopropyl, —CH$_2$-cyclopropyl, cyclopentyl, —(CH$_2$)$_9$CH$_3$, —(CH$_2$)$_6$CH$_3$, CF$_3$, —CH$_2$CF$_3$, —CF$_2$CF$_3$, CCl$_3$, 3-pyridyl, or 4-pyridyl.

For example, $R_{11}$ is $S(O)_2R_a$, and $R_a$ is unsubstituted alkyl (e.g., methyl, ethyl, n-propyl, i-propyl, i-butyl, t-butyl, —(CH$_2$)$_9$CH$_3$, or —(CH$_2$)$_6$CH$_3$).

For example, $R_{11}$ is $S(O)_2R_a$, and $R_a$ is alkyl substituted by one or more halo or $C_3$-$C_8$ cycloalkyl, e.g., —CH$_2$-cyclopropyl, CF$_3$, —CH$_2$CF$_3$, —CF$_2$CF$_3$, or CCl$_3$.

For example, $R_{11}$ is $S(O)_2R_a$, and $R_a$ is optionally substituted phenyl (e.g., phenyl, 2-nitrophenyl).

For example, $R_{11}$ is $S(O)_2R_a$, and $R_a$ is optionally substituted $C_{3-8}$ cycloalkyl (e.g., cyclopropyl or cyclopentyl).

For example, $R_{11}$ is $S(O)_2R_a$, and $R_a$ is optionally substituted 4 to 12-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like).

For example, $R_{11}$ is $S(O)_2R_a$, and $R_a$ is optionally substituted 5 to 14-membered heteroaryl (e.g., pyrrolyl, furyl, thiophenyl, thiazolyl, isothiazolyl, imidazolyl, triazolyl, tetrazolyl, pyrazolyl, oxazolyl, isoxazolyl, pyridyl, pyrazinyl, pyridazinyl, or pyrimidyl).

For example, $R_{11}$ is $S(O)_2R_a$, and $R_a$ is methyl, phenyl, 2-nitrophenyl, n-propyl, propyl, i-butyl, t-butyl, cyclopropyl, —CH$_2$-cyclopropyl, cyclopentyl, —(CH$_2$)$_9$CH$_3$, —(CH$_2$)$_6$CH$_3$, CF$_3$, —CH$_2$CF$_3$, —CF$_2$CF$_3$, CCl$_3$, 3-pyridyl, or 4-pyridyl.

For example, $R_{11}$ is $C(O)_2R_a$, and $R_a$ is unsubstituted alkyl (e.g., methyl, ethyl, n-propyl, i-propyl, i-butyl, t-butyl, —(CH$_2$)$_9$CH$_3$, or —(CH$_2$)$_6$CH$_3$).

For example, $R_{12}$ is $C(O)_2R_a$, and $R_a$ is alkyl substituted by one or more halo or $C_3$-$C_8$ cycloalkyl, e.g., —CH$_2$-cyclopropyl, CF$_3$, —CH$_2$CF$_3$, —CF$_2$CF$_3$, or CCl$_3$.

For example, $R_{11}$ is $C(O)_2R_a$, and $R_a$ is optionally substituted phenyl (e.g., phenyl, 2-nitrophenyl).

For example, $R_{11}$ is $C(O)_2R_a$, and $R_a$ is optionally substituted $C_{3-8}$ cycloalkyl (e.g., cyclopropyl or cyclopentyl).

For example, $R_{11}$ is $C(O)_2R_a$, and $R_a$ is optionally substituted 4 to 12-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like).

For example, $R_{11}$ is $C(O)_2R_a$, and $R_a$ is optionally substituted 5 to 14-membered heteroaryl (e.g., pyrrolyl, furyl, thiophenyl, thiazolyl, isothiazolyl, imidazolyl, triazolyl, tetrazolyl, pyrazolyl, oxazolyl, isoxazolyl, pyridyl, pyrazinyl, pyridazinyl, or pyrimidyl).

For example, $R_{11}$ is $C(O)_2R_a$, and $R_a$ is methyl, phenyl, 2-nitrophenyl, n-propyl, propyl, i-butyl, t-butyl, cyclopropyl, —CH$_2$-cyclopropyl, cyclopentyl, —(CH$_2$)$_9$CH$_3$, —(CH$_2$)$_6$CH$_3$, CF$_3$, —CH$_2$CF$_3$, —CF$_2$CF$_3$, CCl$_3$, 3-pyridyl, or 4-pyridyl.

For example, each of $R_a$ and $R_b$, independently is $C_1$-$C_{20}$ alkyl, $C_2$-$C_{20}$ alkenyl, $C_2$-$C_{20}$ alkynyl, $C_3$-$C_8$ cycloalkyl, $C_6$-$C_{10}$ aryl, 4 to 12-membered heterocycloalkyl, or 5 to 14-membered heteroaryl, each optionally substituted with one or more -Q-T, wherein Q is a bond or $C_1$-$C_3$ alkyl linker each optionally substituted with halo, cyano, hydroxyl or $C_1$-$C_6$ alkoxy, and T is H, halo, cyano, —OR$_c$, —NR$_c$R$_d$, —C(O)R$_c$, —C(O)OR$_c$, —C(O)NR$_c$R$_d$, —NR$_d$C(O)R$_c$, —NR$_d$C(O)OR$_c$, —S(O)$_2$R$_c$, —S(O)$_2$NR$_c$R$_d$, or R$_{S1}$, in which each of R$_c$ and R$_d$, independently is H or R$_{S2}$, each of R$_{S1}$ and R$_{S2}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl; or R$_c$ and R$_d$, together with the N atom to which they are attached, form a 4 to 12-membered heterocycloalkyl ring having 0 or 1 additional heteroatom.

For example, each of $R_a$ independently is methyl or ethyl.

For example, each of $R_a$ independently is methyl or ethyl, each of which is substituted by one or more halo or $C_3$-$C_8$ cycloalkyl.

For example, each of $R_a$ independently is optionally substituted $C_3$-$C_{10}$ alkyl, optionally substituted $C_3$-$C_8$ cycloalkyl, optionally substituted $C_3$-$C_{10}$ alkenyl, optionally substituted $C_3$-$C_{10}$ alkynyl, optionally substituted $C_6$-$C_{10}$ aryl, or optionally substituted 5 to 10-membered heteroaryl.

For example, each of $R_{21}$, $R_{22}$, $R_{23}$, and $R_{24}$, independently, is H or $C_1$-$C_6$ alkyl optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, each of $R_{21}$, $R_{22}$, $R_{23}$, and $R_{24}$, independently, is H or unsubstituted $C_1$-$C_6$ alkyl.

For example, the compound is a compound of any of Formulae (IIIA)-(IIIF).

For example, the compound is a compound of any of Formulae (IIIA)-(IIIF), wherein at least one of $R_{11}$ and $R_{12}$ is $C(O)R_a$ or $S(O)_2R_a$, and $R_a$ is unsubstituted alkyl.

For example, the compound is a compound of any of Formulae (IIIA)-(IIIF), wherein at least one of $R_{11}$ and $R_{12}$ is $C(O)R_a$ or $S(O)_2R_a$, and $R_a$ is substituted alkyl (e.g., alkyl substituted by one or more groups selected from NH$_2$, OH, halo, or $C_1$-$C_6$ alkoxy).

Representative compounds of the present invention include compounds listed in Table 1, in which each of $R_{11}$ and $R_{12}$, independently is H, C(O)R' or S(O)$_2$R', in which R' is methyl, phenyl, 2-nitrophenyl, n-propyl, i-propyl, i-butyl, t-butyl, cyclopropyl, —CH$_2$-cyclopropyl, cyclopentyl, —(CH$_2$)$_9$CH$_3$, —(CH$_2$)$_6$CH$_3$, CF$_3$, —CH$_2$CF$_3$, —CF$_2$CF$_3$, CCl$_3$, 3-pyridyl, or 4-pyridyl, and at most one of $R_{11}$ and $R_{12}$ is H.

TABLE 1
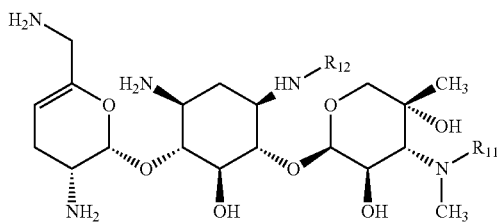
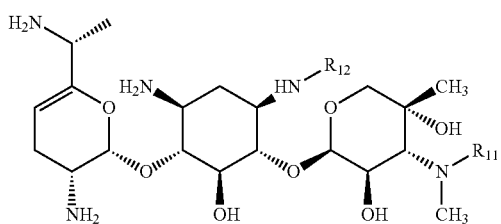
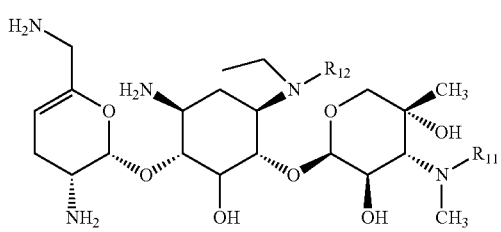
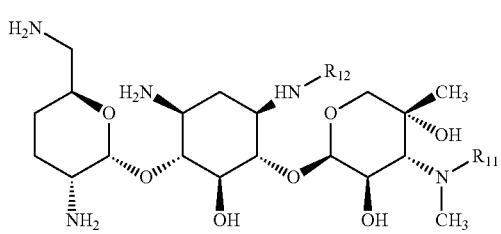
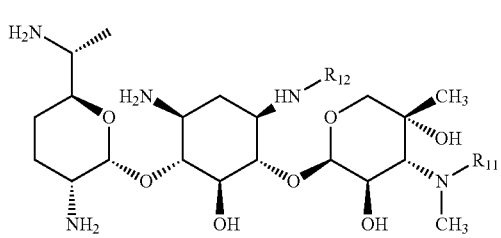
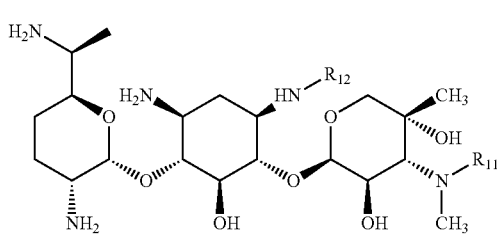
TABLE 1-continued
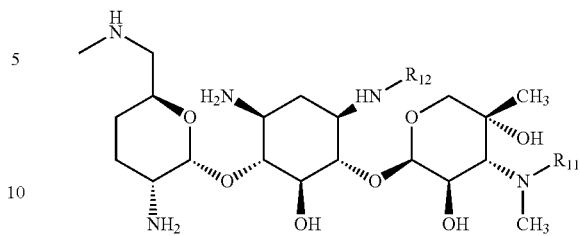
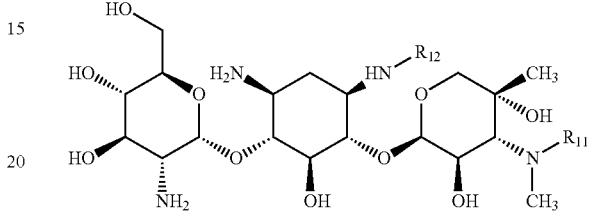
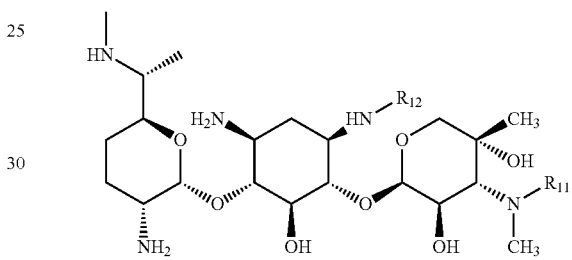
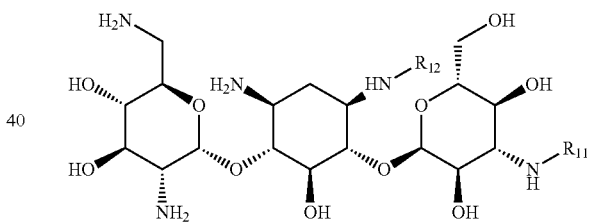
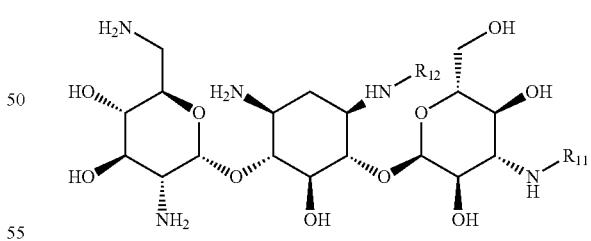
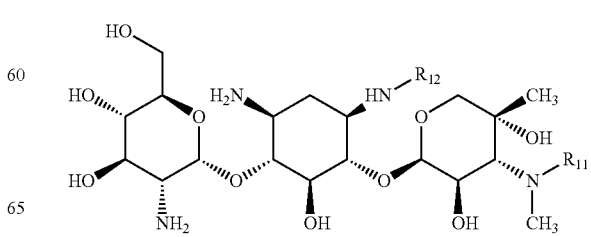

TABLE 1-continued

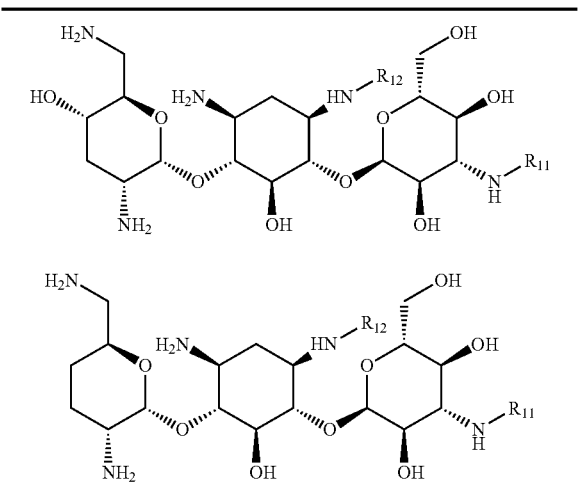

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, and the like.

The term "substituted alkyl" refers to alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ or $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "substituted alkenyl" refers to alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butyryl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "substituted alkynyl" refers to alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, and [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

Other substituted moieties (such as substituted cycloalkyl, heterocycloalkyl, aryl, or heteroaryl) include moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, aryl carbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydrate or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Calm et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms, it being understood that not all isomers may have the same level of activity.

Furthermore, the structures and other compounds discussed in this invention include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine.

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any Formula described herein include the compounds themselves, as well as their salts, their solvates, and their prodrugs, if applicable. A salt, for example, can be formed between an anion and a positively charged group (e.g., amino) on an aminoglycoside compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aminoglycoside compound. Suitable cations include sodium ion, potassium ion, magnesium ion, calcium ion, and an ammonium cation such as tetramethylammonium ion. The aminoglycoside compounds also include those salts containing quaternary nitrogen atoms.

Examples of prodrugs include esters and other pharmaceutically acceptable derivatives, which, upon administration to a subject, are capable of providing active aminoglycoside compounds.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are aminoglycoside compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

Syntheses of Aminoglycoside Derivatives

The present invention provides methods for the synthesis of the compounds of any of the Formulae described herein. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; Greene, T. W., Wuts, P. G. M., *Protective Groups in Organic Synthesis*, $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, $3^{rd}$ edition, John Wiley & Sons: New York, 1999.

Preferred protecting groups include, but are not limited to:
For a hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

In Schemes 1-5 below, variables $R_{11}$ and $R_{12}$ are as defined herein and each of $P_1$, $P_2$, $P_3$, and $P_4$ is an amine protecting groups, e.g. Boc, CBz, PNZ, Nosyl, Ac, CHO, and $CO_2Me$. They can be the same or different. Suitable conditions for the amine-protection and deprotection steps as shown in the schemes below can be found in, e.g., Greene, T. W., Wuts, P. G. M., *Protective Groups in Organic Synthesis*, $3^{rd}$ edition, John Wiley & Sons: New York, 1999, WO2009067692, WO2010132839, WO 2010132777, WO2010132770, and WO 2010147836.

The following abbreviations are used throughout the specification and are defined below:
Ac acetyl
BOC tert-butoxy carbonyl
CBz benzyloxycarbonyl
DMB 2,4 dimethoxybenzyl
Nosyl 2- or 4-nitrobenzenesulfonyl
PNZ p-nitrobenzyloxycarbonyl
TBS tert-butyldimethylsilyl
THP Tetrahydropyranyl Scheme 1 below shows some general routes as to synthesizing dibekacin derivatives with modification(s) at the 1N and/or 3"N positions.

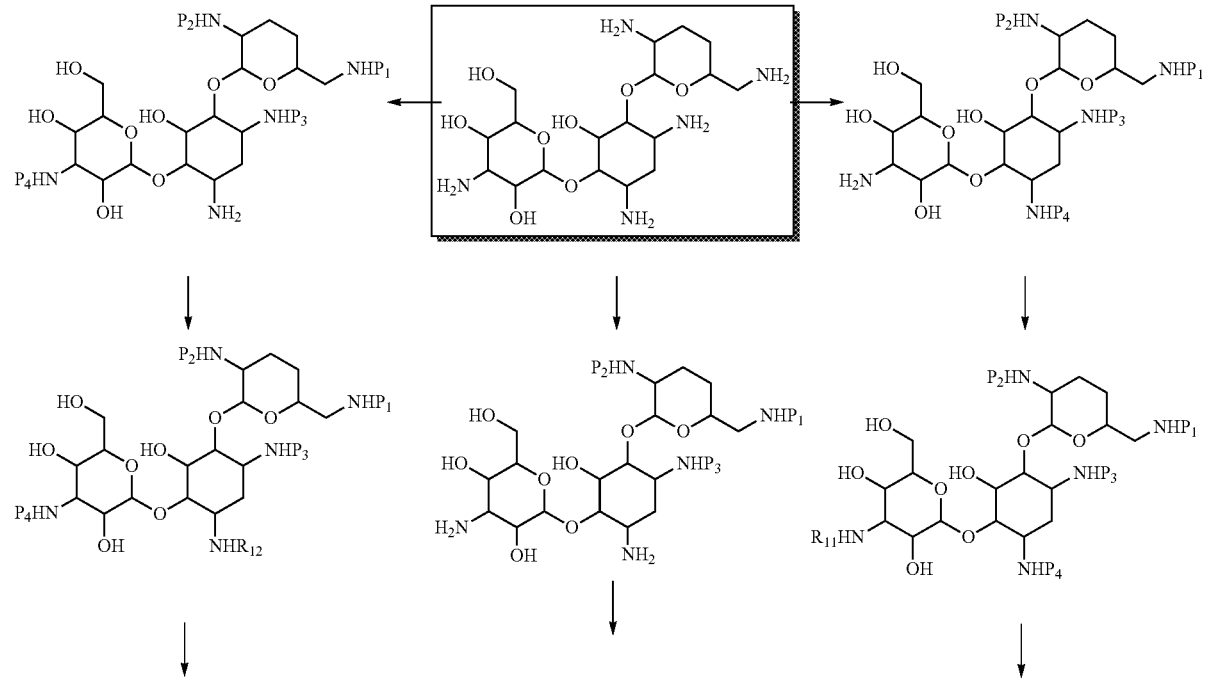

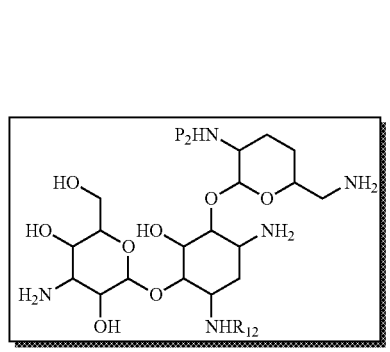
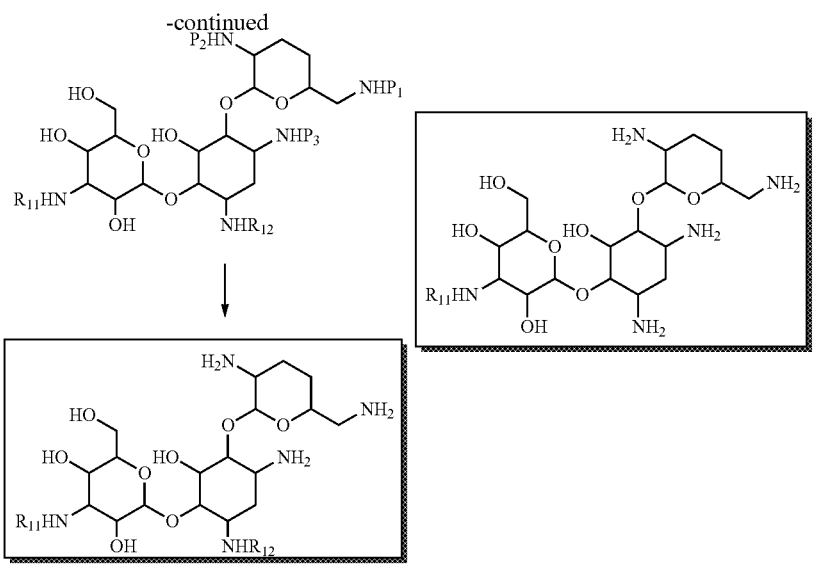
Scheme 2 below shows some general routes as to synthesizing gentamicin derivatives with modification(s) at the 1N and/or 3"N positions.

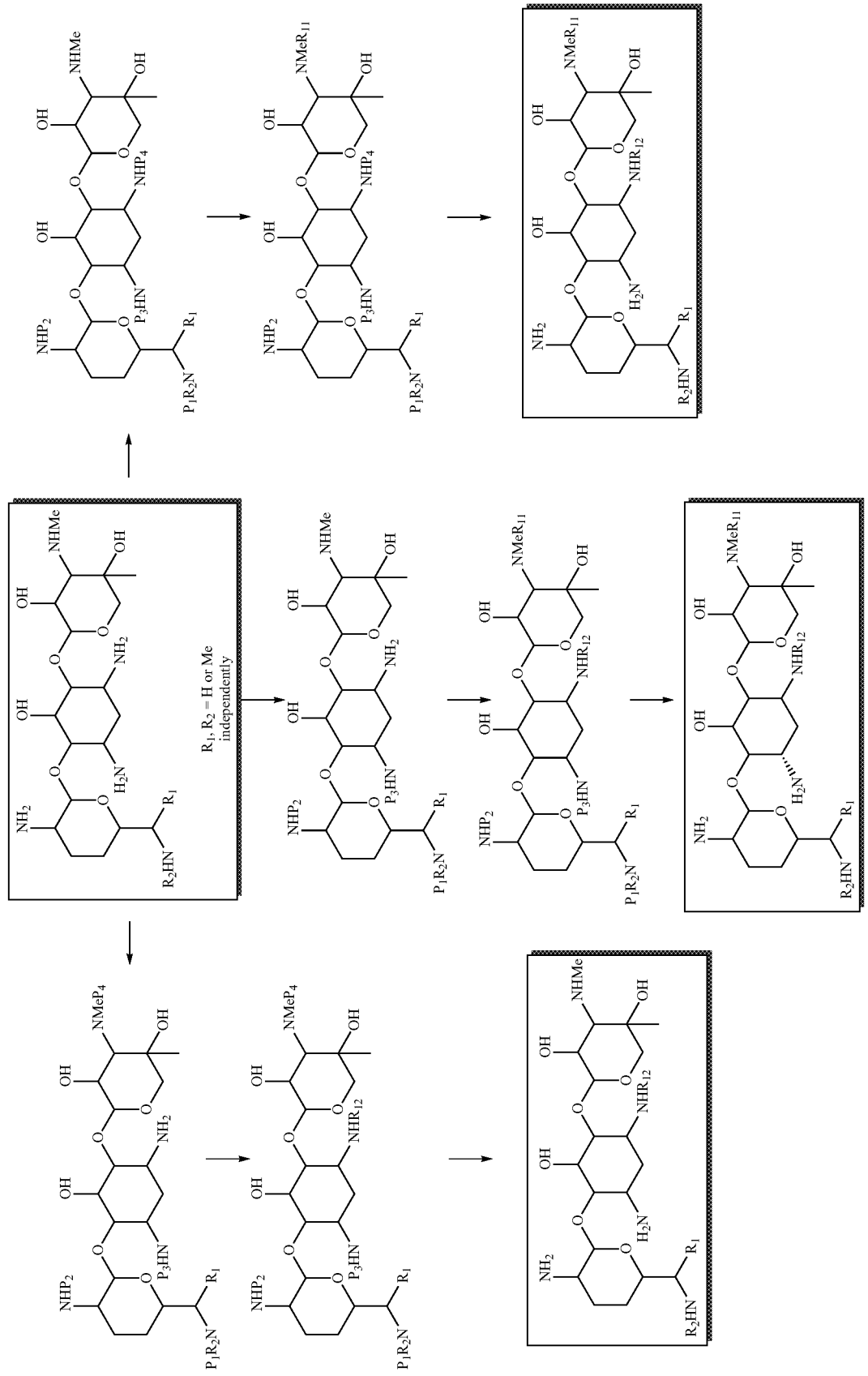

Scheme 3 below shows some general routes as to synthesizing kanamycin derivatives with modification(s) at the 1N and/or 3"N positions.

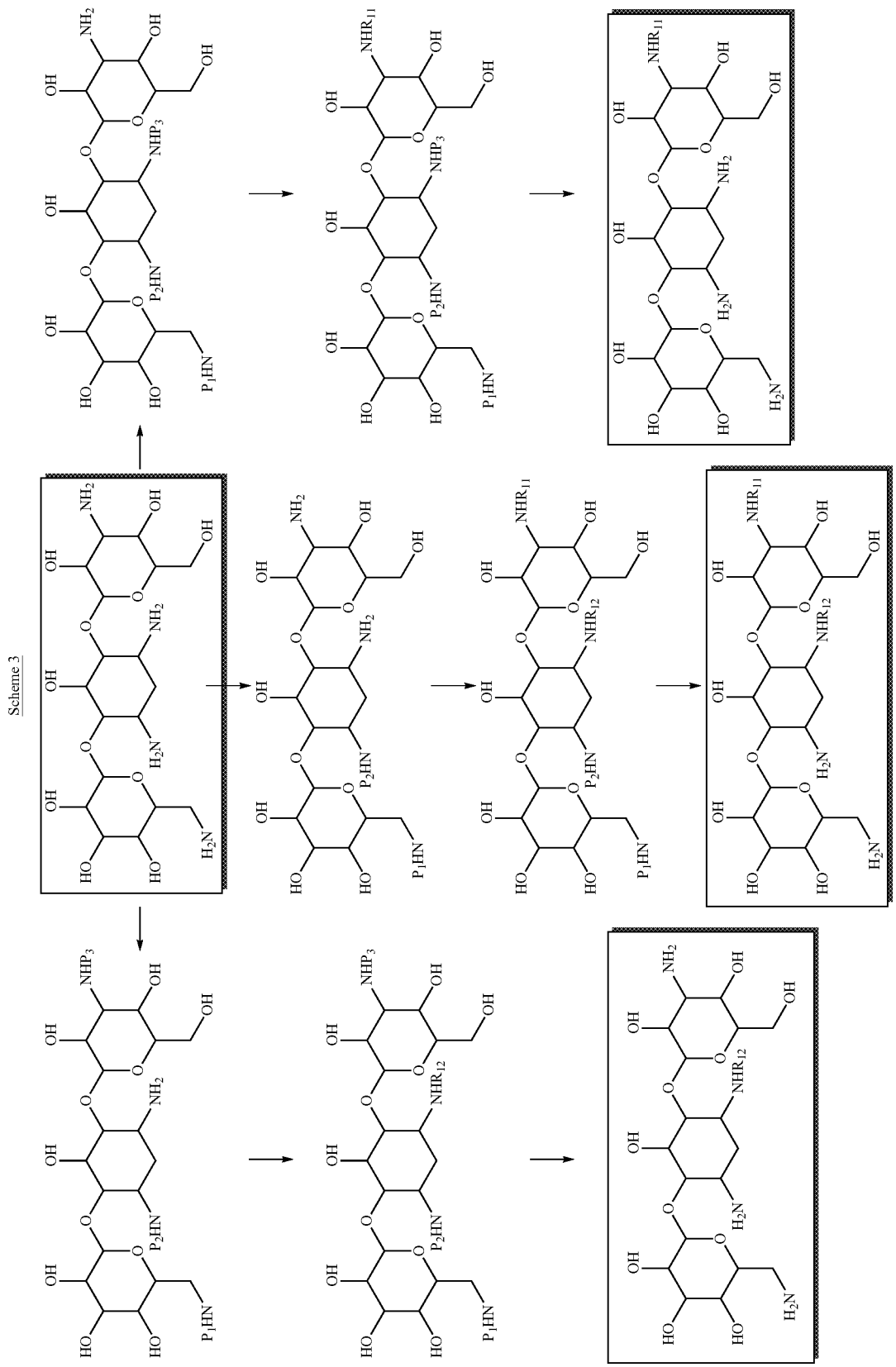

Scheme 4 below shows some general routes as to synthesizing sisomicin derivatives with modification(s) at the 1N and/or 3"N positions.

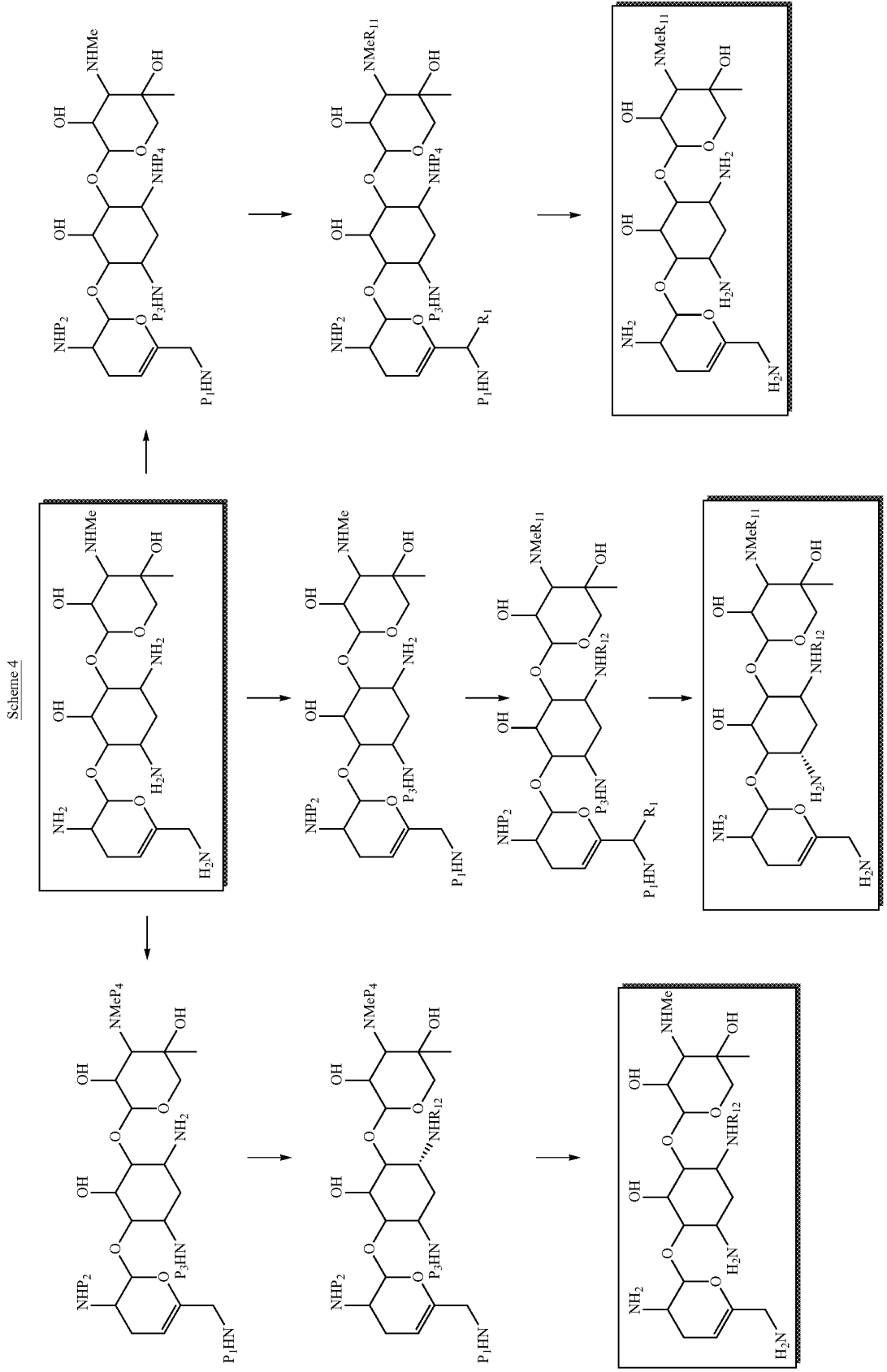

Scheme 5 below shows some general routes as to synthesizing tobramycin derivatives with modification(s) at the 1N and/or 3"N positions.

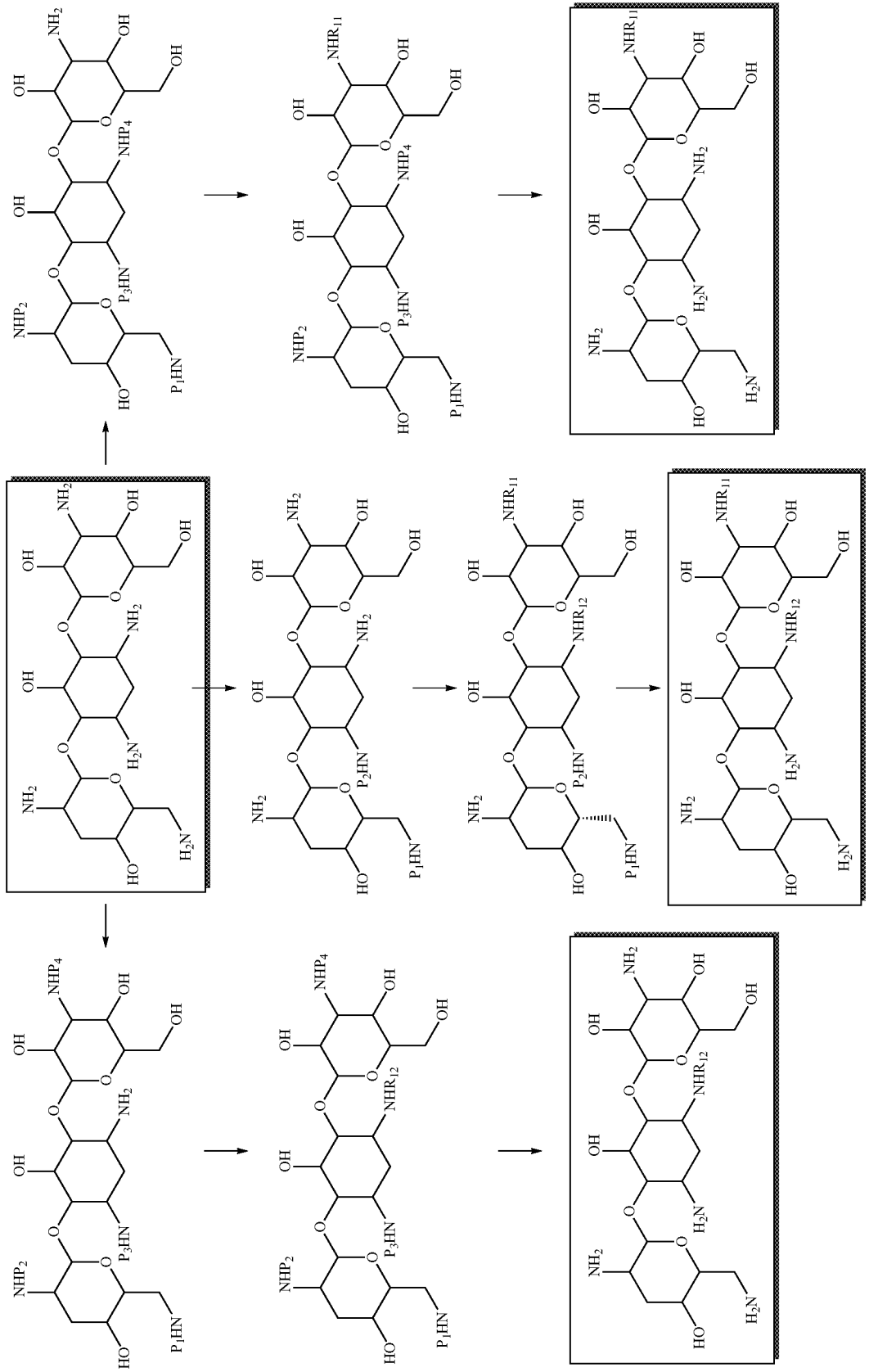

Different salt forms of the aminoglycosides of the invention can be prepared. For example, sulfate salts of the aminoglycosides of the invention can be prepared by the following methods. A non-sulfate salt (e.g., TFA salt of the aminoglycoside) is dissolved in a solvent such as water. Then, a base, e.g., NH$_4$OH is added to raise the pH to about 7. Ammonium sulfate is added. Then the solution is added dropwise to a sufficient amount anti-solvent (e.g., methanol), while, e.g., vigorously stirring the anti-solvent, to precipitate the desired sulfate salt. The resulting solid can be isolated in portions (e.g., 1 mL resulting mixture to a centrifuge tube at a time) by centrifugation, and rinsed with, e.g., methanol.

Pharmaceutical Composition and Administration

The present invention also provides pharmaceutical compositions comprising a compound of any of the Formulae described herein, in combination with at least one pharmaceutically acceptable excipient or carrier, for use in the treatment, amelioration, or prevention of a bacterial infection.

A "pharmaceutical composition" is a formulation containing the compounds of the present invention in a form suitable for administration to a subject.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. A variety of routes are contemplated, including but not limited to, intravenous, intramuscular, topical, oral, pulmonary, rectal, parenteral, intradermal, transdermal, transmucosal, subcutaneousintraperitoneal, inhalational, buccal, sublingual, intrapleural, intranasal, and the like.

For the purposes of administration, the aminoglycosides of the present invention may be administered as a raw chemical or may be formulated as pharmaceutical compositions. Pharmaceutical compositions of the present invention comprise an aminoglycoside and a pharmaceutically acceptable carrier, diluent or excipient. The antibacterial activity of aminoglycosides and compounds of any of the Formulae disclosed herein for various bacteria can be determined by one skilled in the art, for example, as described in the Examples below. Appropriate concentrations and dosages can be readily determined by one skilled in the art.

Administration of aminoglycosides, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term "parenteral" as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: *The Science and Practice of Pharmacy*, 20th Edition (Philadelphia College of Pharmacy and Science, 2000).

The pharmaceutical composition may be in the form of a liquid, for example, an elixir, syrup, solution, emulsion or suspension. The liquid may be for oral administration or for delivery by injection, as two examples. In a composition intended to be administered by injection, one or more of a surfactant, preservative, wetting agent, dispersing agent, suspending agent, buffer, stabilizer and isotonic agent may be included. The parenteral preparation can be enclosed in ampoules, disposable syringes or multiple dose vials made of glass or plastic. Physiological saline is a preferred adjuvant. An injectable pharmaceutical composition is preferably sterile.

The aminoglycosides, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Aminoglycosides, or pharmaceutically acceptable derivatives thereof, may also be administered simultaneously with, prior to, or after administration of one or more other therapeutic agents. Such combination therapy includes administration of a single pharmaceutical dosage formulation which contains an aminoglycoside and one or more additional active agents, as well as administration of the aminoglycoside and each active agent in its own separate pharmaceutical dosage formulation.

Pharmaceutical carriers suitable for administration of the compounds and biologics provided herein include any such carriers known to those skilled in the art to be suitable for the particular mode of administration including those described herein. The compounds may be formulated as the sole pharmaceutically active ingredient in the composition or may be combined with other active ingredients.

Compositions comprising the compounds disclosed herein may be suitable for oral, rectal, nasal, topical (including buccal and sublingual), vaginal, or parenteral (including subcutaneous, intramuscular, subcutaneous, intravenous, intradermal, intraocular, intratracheal, intracisternal, intraperitoneal, and epidural) administration.

The compositions may conveniently be presented in unit dosage form and may be prepared by conventional pharmaceutical techniques. Such techniques include the step of bringing into association one or more compositions provided herein and one or more pharmaceutical carriers or excipients.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof may be mixed with one or more suitable pharmaceutical carriers. The compounds may be derivatized as the corresponding salts, esters, enol ethers or esters, acetals, ketals, orthoesters, hemiacetals, hemiketals, acids, bases, solvates, hydrates or prodrugs prior to formulation. The concentrations of the compounds in the compositions are effective for delivery of an amount, upon administration, that treats, prevents, or ameliorates one or more of the symptoms of the target disease or disorder. In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

Compositions suitable for oral administration may be presented as discrete units such as, but not limited to, tablets, caplets, pills or dragees capsules, or cachets, each containing a predetermined amount of one or more of the compositions; as a powder or granules; as a solution or a suspension in an aqueous liquid or a non-aqueous liquid; or as an oil-in-water liquid emulsion or a water-in-oil emulsion or as a bolus, etc.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents, preservatives, flavoring agents, and the like, for example, acetate, sodium citrate, cyclodextrin derivatives, sorbitan monolaurate, triethanolamine sodium acetate, triethanolamine oleate, and other such agents. Methods of preparing such dosage forms are known, or will be apparent, to those skilled in this art; for example, see Remington's Pharmaceutical Sciences, Mack Publishing Company, Easton, Pa., 15th Edition, 1975.

Compositions of the present invention suitable for topical administration in the mouth include for example, lozenges, having the ingredients in a flavored basis, usually sucrose and acacia or tragacanth; pastilles, having one or more of the compositions of the present invention in an inert basis such as gelatin and glycerin, or sucrose and acacia; and mouthwashes, having one or more of the compositions of the present invention administered in a suitable liquid carrier.

The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, *lycopodium* and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Compositions suitable for topical administration to the skin may be presented as ointments, creams, gels, and pastes, having one or more of the compositions administered in a pharmaceutical acceptable carrier.

Compositions for rectal administration may be presented as a suppository with a suitable base comprising, for example, cocoa butter or a salicylate.

Compositions suitable for nasal administration, when the carrier is a solid, include a coarse powder having a particle size, for example, in the range of 20 to 500 microns which is administered in the manner in which snuff is taken, (i.e., by rapid inhalation through the nasal passage from a container of the powder held close up to the nose). When the carrier is a liquid (for example, a nasal spray or as nasal drops), one or more of the compositions can be admixed in an aqueous or oily solution, and inhaled or sprayed into the nasal passage.

Compositions suitable for vaginal administration may be presented as pessaries, tampons, creams, gels, pastes, foams or spray formulations containing one or more of the compositions and appropriate carriers.

Compositions suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The compositions may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets of the kind previously described above.

Pharmaceutical organic or inorganic solid or liquid carrier media suitable for enteral or parenteral administration can be used to fabricate the compositions. Gelatin, lactose, starch, magnesium stearate, talc, vegetable and animal fats and oils, gum, polyalkylene glycol, water, or other known carriers may all be suitable as carrier media.

Additionally, the compositions may be combined with pharmaceutically acceptable excipients, and, optionally, sustained-release matrices, such as biodegradable polymers, to form therapeutic compositions.

Compositions are preferably formulated in dosage unit form for ease of administration and uniformity of dosage. "Dosage unit form" as used herein refers to a physically discrete unit of the composition appropriate for the host to be treated. Each dosage should contain the quantity of composition calculated to produce the desired therapeutic affect either as such, or in association with the selected pharmaceutical carrier medium.

Exemplary unit dosage formulations are those containing a daily dose or unit, daily sub-dose, or an appropriate fraction thereof, of the administered ingredient. The dosage will depend on host factors such as weight, age, surface area, metabolism, tissue distribution, absorption rate and excretion rate.

The therapeutically effective dose level will depend on many factors as noted above. In addition, it is well within the skill of the art to start doses of the composition at relatively low levels, and increase the dosage until the desired effect is achieved.

Compositions comprising a compound disclosed herein may be used with a sustained-release matrix, which can be made of materials, usually polymers, which are degradable by enzymatic or acid-based hydrolysis or by dissolution. Once inserted into the body, the matrix is acted upon by enzymes and body fluids. A sustained-release matrix for example is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho) esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (copolymers of lactic acid and glycolic acid).

The compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The liposome can contain, in addition to one or more compositions of the present invention, stabilizers, preservatives, excipients, and the like. Examples of lipids are the phospholipids and the phosphatidyl cholines (lecithins), both natural and synthetic. Methods to form liposomes are known in the art.

The compounds may be formulated as aerosols for application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compound or composition is present in the pharmaceutical composition in an amount which is effective to treat a particular disease or condition of interest, that is, in an amount sufficient to treat a bacterial infection, and preferably with acceptable toxicity to the patient. The antibacterial activity of the compounds and compositions disclosed herein can be determined by one skilled in the art, for example, as described in the Examples below. Appropriate concentrations and dosages can be readily determined by one skilled in the art. The compounds and compositions disclosed herein possess antibacterial activity against a wide spectrum of gram positive and gram negative bacteria, as well as enterobacteria and anaerobes. Representative susceptible organisms generally include those gram positive and gram negative, aerobic and anaerobic organisms whose growth can be inhibited by the compounds and compositions disclosed herein such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella, Francisella, Anthracis, Yersinia, Corynebacterium, Moraxella, Enterococcus*, and other organisms. For example, representative bacterial infections that may treated according to methods of the invention include, but are not limited to, infections of: *Bacillus anthracis; Enterococcus faecalis; Corynebacterium; diphtheriae; Escherichia coli; Streptococcus coelicolor; Streptococcus pyogenes; Streptobacillus moniliformis; Streptococcus agalactiae; Streptococcus pneumoniae; Salmonella typhi; Salmonella paratyphi; Salmonella schottmulleri; Salmonella hirshfeldii; Staphylococcus epidermidis; Staphylococcus aureus; Klebsiella pneumoniae; Legionella pneumophila; Helicobacter pylori; Moraxella catarrhalis, Mycoplasma pneumonia; Mycobacterium tuberculosis; Mycobacterium leprae; Yersinia enterocolitica; Yersinia pestis; Vibrio cholerae; Vibrio parahaemolyticus; Rickettsia prowazekii; Rickettsia rickettsii; Rickettsia akari; Clostridium difficile; Clostridium tetani; Clostridium perfringens; Clostridium novyii; Clostridium septicum; Clostridium botulinum; Legionella pneumophila; Hemophilus influenzae; Hemophilus parainfluenzae; Hemophilus aegyptus; Chlamydia psittaci; Chlamydia trachomatis; Bordetella pertusis; Shigella* spp.; *Campylobacter jejuni; Proteus* spp.; *Citrobacter* spp.; *Enterobacter* spp.; *Pseudomonas aeruginosa; Propionibacterium* spp.; *Bacillus anthracis; Pseudomonas syringae; Spirrilum minus; Neisseria meningitidis; Listeria monocytogenes; Neisseria gonorrheae; Treponema pallidum; Francisella tularensis; Brucella* spp.; *Borrelia recurrentis; Borrelia hermsii; Borrelia turicatae; Borrelia burgdorferi; Mycobacterium avium; Mycobacterium smegmatis*; Methicillin-resistant *Staphylococcus aureus*; Vancomycin non-susceptible *Staphylococcus aureus*; Vancomycin-resistant *enterococcus*; drug resistant *Pseudomonas aeruginosa* (such as, for example, doripenem resistant *Pseudomonas aeruginosa*, imipenem resistant *Pseudomonas aeruginosa*, cefepime resistant *Pseudomonas aeruginosa*, and piperacillin/tazobactam resistant *Pseudomonas aeruginosa*); and multi-drag resistant bacteria (e.g., bacteria that are resistant to more than 1, more than 2, more than 3, or more than 4 different drugs).

The compounds of the present invention, or pharmaceutically acceptable salts, prodrugs, metabolites, polymorphs or solvates thereof, have been or will be tested in one or more in vitro or in vivo biological assays, in order to determine if these compounds are likely to elicit a desired biological or medical response in a cell, tissue, system, animal or human that is being sought by a researcher or clinician. The biological or medical response can be the treatment of a bacterial infection with little or no ototoxicity or nephrotoxicity. The biological response or effect can also include a change in bacterial growth that occurs in vitro or in an animal model, as well as other biological changes that are observable in vitro. In vitro or in vivo biological assays can include, but are not limited to, Minimum Inhibitory Concentration Test (MIC), Minimum Bactericidal Concentration (MB C) Test, Auditory brainstem responses (ABR), distortion product otoacoustic emissions (DPOAEs), ototoxicity test described in, e.g., Alharazneh et al., 2011, and the assays described herein.

For example, an ototoxicity test that can be used includes the steps of (1) treating organ of corti cultures with a compound of the invention and a parent aminoglycoside compound for a certain period of time (e.g., 1 hour), respectively; (2) washing and then culturing the treated tissue for some period of time (e.g., 2 days); (3) fixing and staining the tissue so that hair cell counts can be obtained; and (4) comparing the hair cell counts between the tissue treated by the compound of the invention and the tissue treated by the parent aminoglycoside compound.

For example, a mouse model is developed for ototoxicity analysis. Test compound, combined with furosemide as co-treatment, is administered to the mice. Auditory brainstem responses (ABR) as well as distortion product otoacoustic emissions (DPOAEs) is measured prior to treatments and 1 week following a single high dose of test compound administered intraperitoneally concomitantly with a single dose of furosemide. Data are then collected and analyzed.

Compositions comprising the compounds disclosed herein may be used in combination with other compositions and/or procedures for the treatment of the conditions described herein.

Combination Therapy

The method of treating the patient may involve administering, in addition to the aminoglycoside compounds of the invention, at least one additional active agent, such as a second antibacterial agent, e.g., daptomycin (DAP), ceftobiprole (BPR), or linezolid (LZD).

In one embodiment, the additional active agent comprises the parent aminoglycoside compounds. In certain embodiments, one or more aminoglycoside compounds of the invention (e.g., sisomicin derivatives or gentamicin derivatives), when co-administered with the parent aminoglycoside (e.g., sisomicin or gentamicin, respectively), reduce the toxic (e.g., ototoxic or nephrotoxic) effects of the parent aminoglycoside, regardless of the antibacterial activity of the aminoglycoside derivatives.

As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

In one embodiment, the aminoglycoside compounds of the invention can be used concurrently with known aminoglycosides to reduce ototoxicity of the known compounds.

"Combination therapy" also embraces the administration of the therapeutic agents as described above in further combination with other biologically active ingredients and non-drug therapies (e.g., surgery or physical therapy). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As used herein, "monotherapy" refers to the administration of a single active or therapeutic compound to a subject in need thereof. Preferably, monotherapy will involve administration of a therapeutically effective amount of an active compound. Monotherapy may be contrasted with combination therapy, in which a combination of multiple active compounds is administered, preferably with each component of the combination present in a therapeutically effective amount. Monotherapy with a compound of the present invention, or a pharmaceutically acceptable salt, prodrug, metabolite, polymorph or solvate thereof, may be more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, prodrug, metabolite, polymorph or solvate thereof, can or may also be used to prevent a bacterial infection. As used herein, "preventing" or "prevent" describes reducing or eliminating the onset of the symptoms or complications of such disease, condition or disorder.

As used herein, a "subject" is interchangeable with a "subject in need thereof", both of which refers to a subject having a bacterial infection or a subject having an increased risk of developing such infection relative to the population at large such as immunosuppressed patients. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. For example, a subject is an infant, a pediatric patient, or a pregnant woman.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

All percentages and ratios used herein, unless otherwise indicated, are by weight. Other features and advantages of the present invention are apparent from the different examples.

The provided examples illustrate different components and methodology useful in practicing the present invention. The examples do not limit the claimed invention. Based on the present disclosure the skilled artisan can identify and employ other components and methodology useful for practicing the present invention.

EXAMPLES

Preparative Examples

Sisomicin

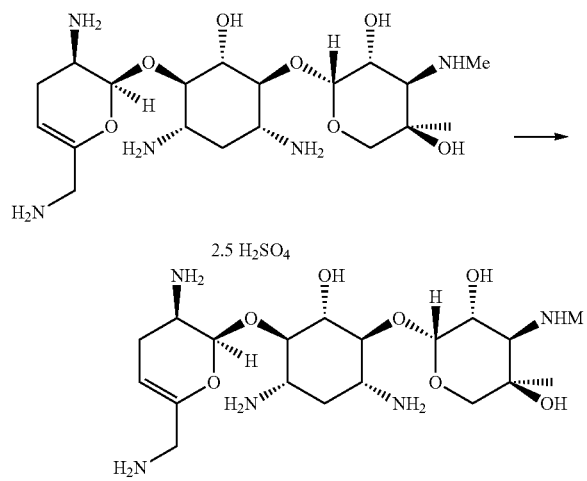

Amberlite IRA-400 (OH form) (1200 g) was washed with MeOH (3×1200 ml). To a stirring suspension of the washed resin in MeOH (900 mL) was added sisomicin sulfate (120.0 g) and the mixture was stirred 2 days. The resin was then filtered and washed with MeOH (600 mL) and the combined organic layers were concentrated to dryness to yield the desired sisomicin (60 g).

PNZ-Protective Group

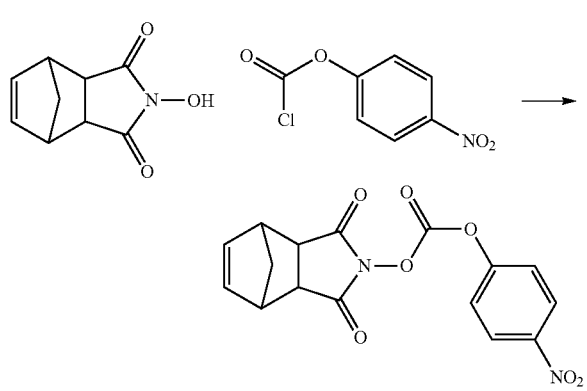

To a stirring solution of 4-nitrobenzyl chloroformate (27.40 g) in THF (500 mL) at 0° C. was added N-hydroxy-5-norbornene-2,3-dicarboximide (22.76), followed by the dropwise addition of a solution of $Et_3N$ (17.72 ml) in THF (200 mL) and the reaction was stirred for overnight with gradual warming to room temperature. The reaction vessel was then placed in the freezer (−5° C.) for 1 hour to induce precipitation of triethylamine hydrochloride, which was removed by filtration. The filtrate was concentrated to dryness to yield a residue, which was vigorously stirred in MeOH (400 mL) for 1 h and then filtered to yield (N-hydroxy-5-norbornene-2,3-dicarboxyl-imido)-4-nitro-benzoate as a white solid (42.03 g, yield: 92%).

General Procedures
General Procedure for Nosylation

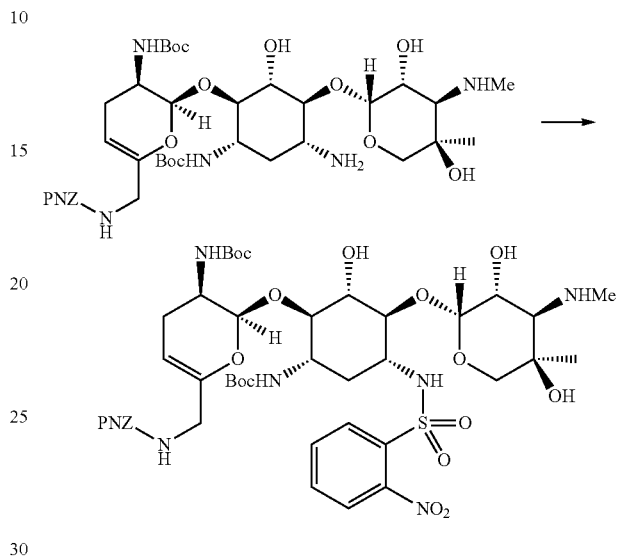

To a stirring solution of 6'-PNZ, 2',3-diBoc-sisomicin (1.5 mmol) in 15 ml chloroform and 15 ml 5% Sodium Bicarbonate solution was added 2-nitrobenzenesulfonyl chloride (1.68 mmol), and the reaction was allowed to stir for 1.5 hours. The reaction progress was monitored by LC-MS. Upon completion, the reaction mixture was diluted with chloroform and was washed with saturated sodium bicarbonate and brine solution. After evaporation of solvent, the reaction mixture was purified by HPLC. The product was obtained as an off-white solid. (M+H=1013).

General Procedure for De-Nosylation

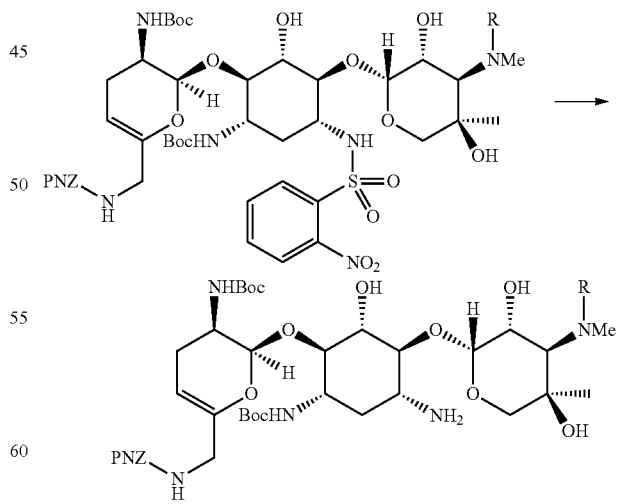

To a stirring solution of the nosyl protected sisomicin derivative (0.12 mmol) in acetonitrile (5 mL) was added benzenethiol (0.24 mmol), $K_2CO_3$ (0.36 mmol) and the reaction mixture was stirred for 2 hours at room temperature, with its progress monitored by MS. Upon completion, the reaction mixture was diluted with water (5 mL) and extracted with chloroform (2×10 mL). The combined organic layers were washed with water (2×5 mL) and brine (5 mL), dried over $Na_2SO_4$, filtered and concentrated to dryness, purified through silica gel chromatography with 5% MeOH in dichloromethane with 0.1% $Et_3N$. Note that the R group in the scheme above has the same definition as $R_{11}$ in any of the relevant Formulae described herein.

General Procedure for Boc Deprotection

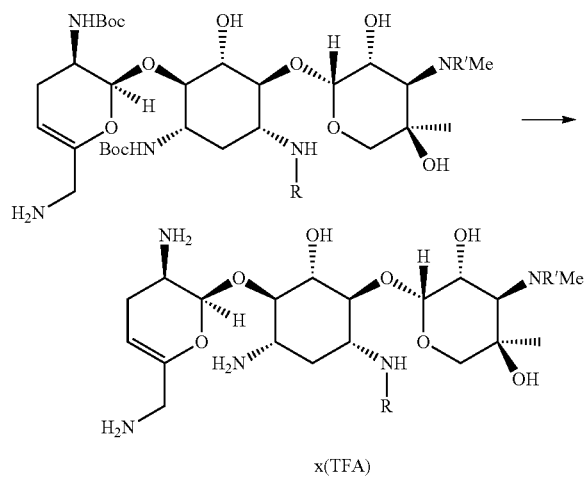

Before Boc deprotection, a sample must be dried well by pumping at high vacuum for 3 h.

To a stirring solution of the Boc protected sisomicin (0.054 mmol) in DCM (1 mL) were added trifluoroacetic acid (0.6 mL). The reaction was stirred at room temperature for 1 h, and checked for completeness by MS. Upon completion the reaction mixture was. Evaporated off, 5-10 mL H2O was added and after dried over lyophilization. Note that the R' group in the scheme above has the same definition as $R_{11}$ in any of the relevant Formulae described herein.

General Procedure for PNZ Deprotection

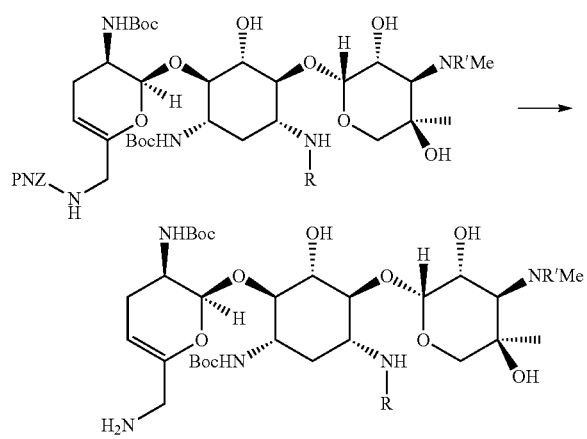

To a stirring solution of the PNZ protected sisomicin derivative (0.054 mmol) in EtOH (1.5 mL) and $H_2O$ (1 mL) was added 1N NaOH (0.3 mL), followed by $Na_2S_2O_4$ (0.315 mmol), and the reaction mixture was heated at 70° C. for 6 hours. The reaction progress was monitored by MS. Once reaction was completed, the reaction mixture was diluted with $H_2O$ (5 mL) and then extracted with EtOAc (2×10 mL). The combined organic layers were washed with $H_2O$ (2×5 mL), brine (5 mL), dried over $Na_2SO_4$, filtered and concentrated to dryness. Note that the R' group in the scheme above has the same definition as $R_{11}$ in any of the relevant Formulae described herein.

Provided below are examples of benzenesulfonyl, methyl sulfonyl and/or benzoyl substitutions at the 1N-position, 3"N-position, or 1N- and 3"N-positions of sisomicin. For each of these compounds, the first step was the PNZ protection followed by the Boc protection as outlined below.

Example 1

6'-PNZ-sisomicin

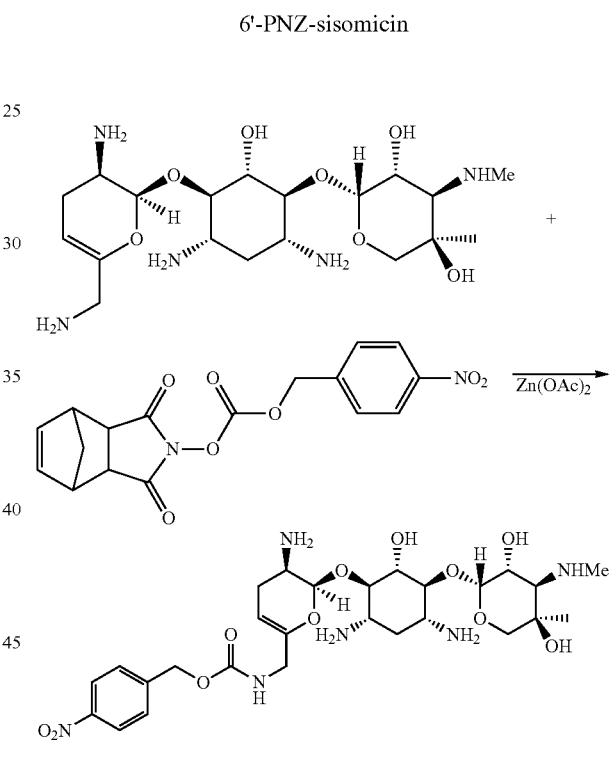

To a stirring solution of sisomicin (15.00 g) in MeOH (300 mL) was added $Zn(OAc)_2$ (18.44 g) and the reaction mixture was stirred for 1 hour until all the zinc had gone into solution. A solution of (N-hydroxy-5-norbornene-2,3-dicarboxyl-imido)-4-nitro-benzoate (11.77 g) was then added over 20 mins and the reaction was allowed to stir overnight. The reaction was then concentrated to dryness; the crude product was slowly added to a vigorously stirring solution of 10% aq $NH_4OH$ (255 mL).

The aqueous layer was separated, washed with DCM (3×125 mL), and diluted with brine (75 mL). The aqueous layer was extracted with DCM IPA (7 3 v/v, 3×250 mL). The combined organic layers were washed with 10% aq $NH_4OH$/brine (7 3 v/v, 250 mL), dried over $MgSO_4$, filtered and concentrated to yield the desired 6'-PNZ-sisomicin (7.98 g).

Example 2

6'-PNZ-2°,3-diBoc-sisomicin

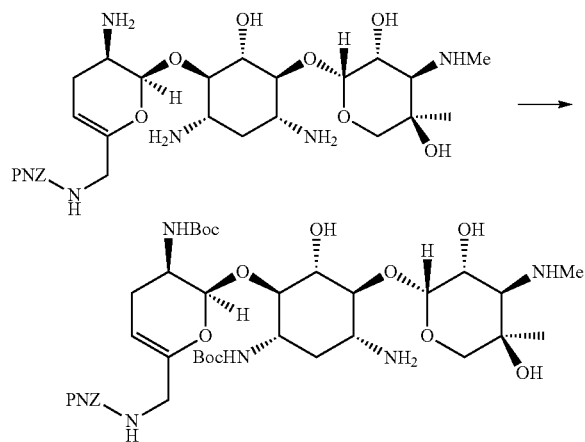

To a stirring solution of 6'-PNZ-sisomicin (5.0 g) in MeOH (50 mL) was added Zn(OAc)$_2$ (2.93 g) and the reaction mixture was stirred for 4 hours until all solids had dissolved. A solution of Boc anhydride (3.83 g) and Triethylamine (3.3 mL) in THF (50 mL) was added dropwise over 1 hour and the reaction mixture was allowed to stir overnight. The solvent was removed by rotary evaporation to yield a residue, which was added in conc. NH$_4$OH (20 mL) and ethanol (30 mL). It was extracted with chloroform (3×50 mL). The organic layer was dried over MgSO$_4$, filtered and concentrated to dryness and purified by silica gel chromatography to yield the desired 6'-PNZ-2',3-diBoc-sisomicin (4.0 g). This product was the major intermediary starting material for all selective modifications presented.

Example 3

1-Benzenesulfonyl-sisomicin

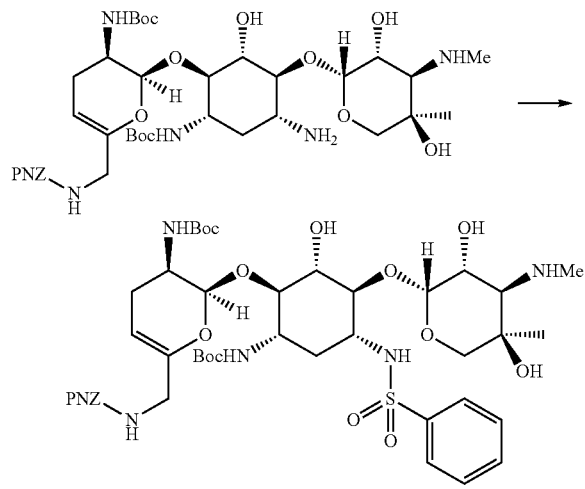

To a stirring solution of 6'-PNZ, 2',3-diBoc-sisomicin (0.49 mmol, 0.407 g) in 4 ml chloroform and 4 ml 5% Sodium Bicarbonate solution was added Benzenesulfonyl chloride (0.54 mmol), and the reaction was allowed to stir for 5 minutes at 0° C. and 20 min at room temperature. The reaction progress was monitored by LC-MS. Upon completion, the reaction mixture was diluted with chloroform and was washed with saturated sodium bicarbonate and brine solution. After evaporation of solvent, the reaction mixture was purified by HPLC. The product was obtained as an off-white solid (0.193 g). This product was then de-Boc'ed to obtain the final product following the general procedure for removing the boc protective group.

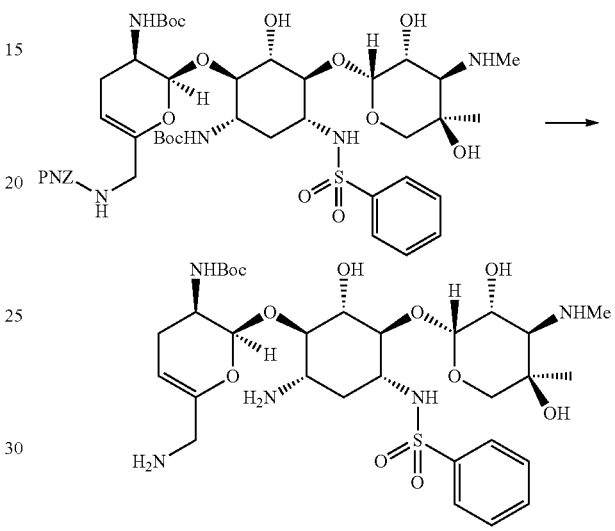

40 mg 1-Benzenesulfonyl-sisomicin was obtained after HPLC purification from 0.193 g 6'-PNZ-2',3-diBoc-1-Benzenesulfonyl-sisomicin following the general procedure for PNZ deprotection and the general procedure for Boc deprotection. PNZ deprotection was performed at room temperature and was completed at 1 hour; the product was purified by silica gel chromatograph (5% MeOH in chloroform with 0.1% Et$_3$N).

Example 4

1,3''-dibenzenesulfonyl-sisomicin

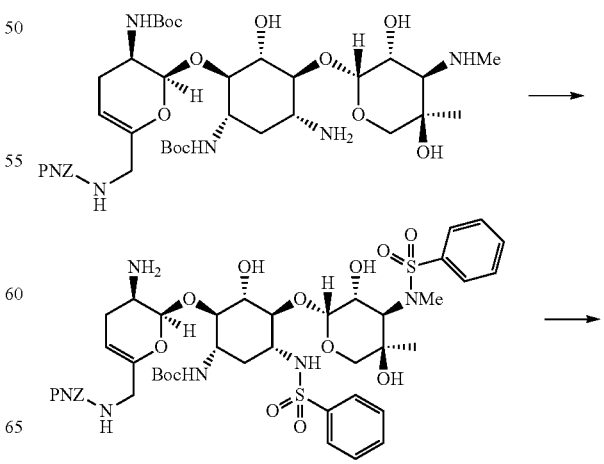

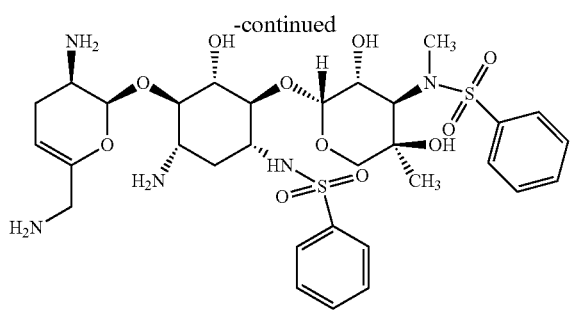

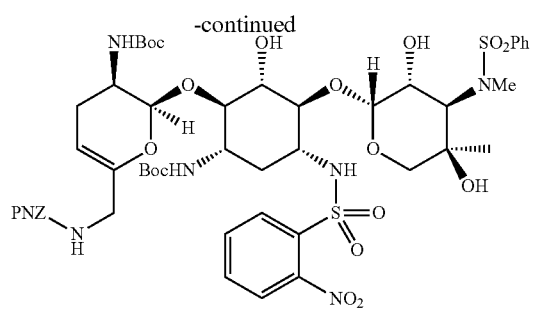

0.350 g 6'-PNZ-2',3-diBoc-1,3"-dibenzenesulfonyl-sisomicin was obtained following the procedure for 6'-PNZ-2',3-diBoc-1-Benzenesulfonyl-sisomicin from 0.726 g 6'-PNZ-2',3-diBoc-sisomicin and 2.1 eq Benzenesulfonyl chloride stirred overnight. 0.173 g 1,3"-dibenzenesulfonyl-sisomicin was obtained from 0.350 g 6'-PNZ-2',3-diBoc-1,3"-dibenzenesulfonyl-sisomicin following the same procedures for PNZ deprotection and Boc deprotection as described above.

Example 5

3"-benzenesulfonyl-sisomicin

From 1.033 g 6'-PNZ-2',3-diBoc-sisomicin, following the general procedure for nosylation, 0.499 g 6'-PNZ-2',3-diBoc-1-Nosyl-sisomicin was obtained as yellow solid after HPLC purification.

This product is then sequentially denosylated and then de-boc'ed and the PNZ deprotected as follows:

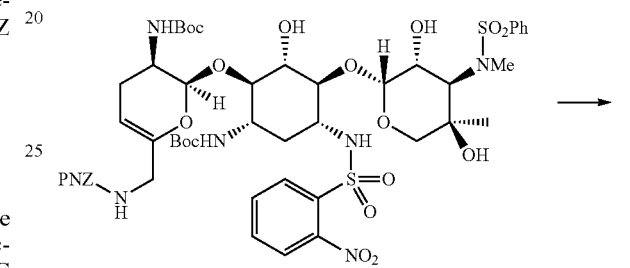

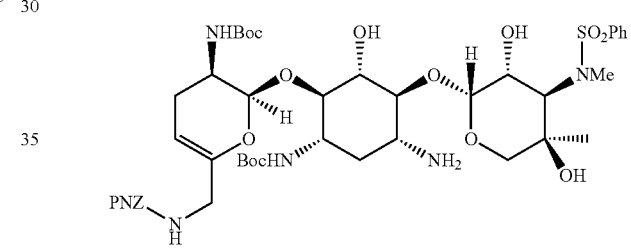

Following the general procedure for de-Nosylation, 0.100 g title compound was obtained as white solid after HPLC purification from 0.143 g 6'-PNZ-2',3-diBoc-1-Nosyl-3"-Benzenesulfonyl sisomicin.

Then the product is PNZ deprotected as:

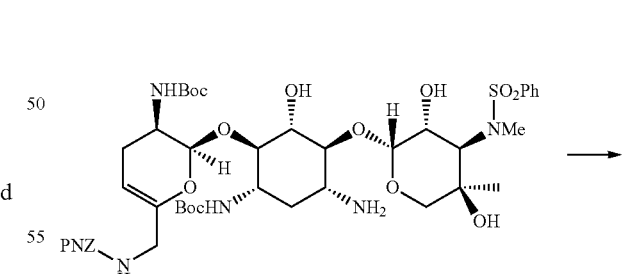

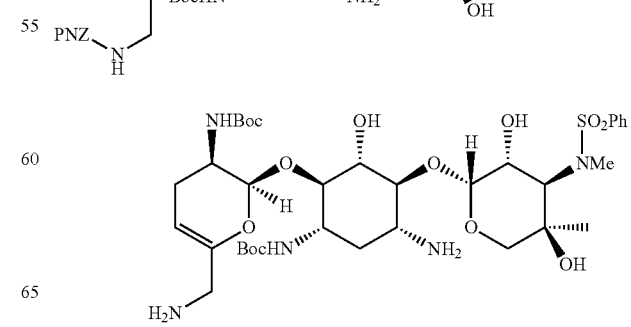

At this point the product was sulfonylated as described previously.

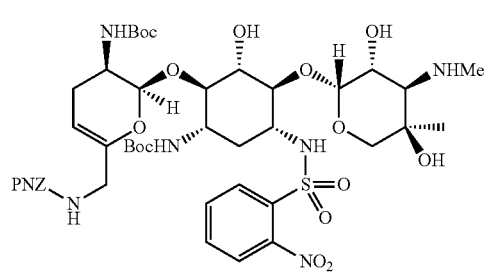

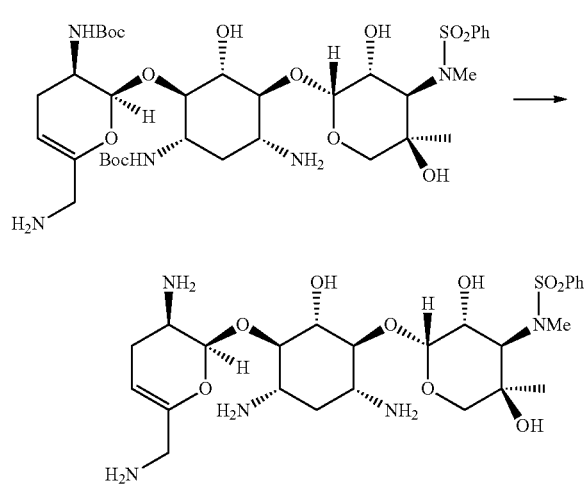

Following the general procedure for de-Boc, 54 mg title compound TFA salt was obtained as yellow solid after HPLC purification from 48 mg 2',3-diBoc-3"-Benzenesulfonyl sisomicin.

Example 6

Other Sisomicin Derivatives

Sisomicin was modified with other substituents such as a Benzoyl group or a methyl sulfonyl group via methods similar to those described in Examples 1-5.

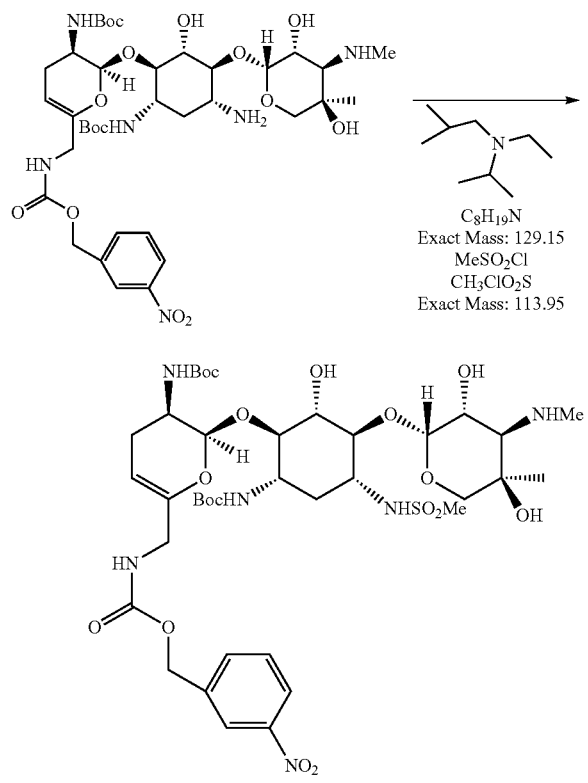

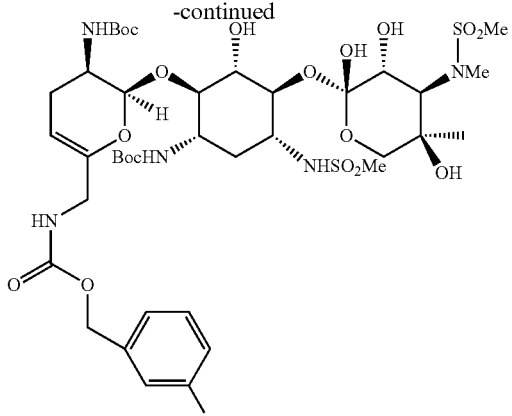

1-N-methysulfonyl sisomicin and 1,3"-N-methylsulfonyl sisomicin were prepared from the starting material of boc protected and PNZ protected substrate. 6'-PNZ-3,2'-diboc-sisomicin (0.400 g, 0.48 mmol) was dissolved in chloroform (8 mL). Diisopropylethyl amine (0.150 mg, 1.16 mmol) was added followed by methane sulfonyl chloride (0.085 g, 0.75 mmol). The mixture was stirred at room temperature for 6 h. HPLC analysis showed the presence of mono- and di-sulfonylated products which were isolated by removal of the solvent and purification by HPLC. Treatment of each compound by the general procedure described for PNZ and Boc deprotection gave 70 mg each of 1-N-methylsulfonyl sisomicin $C_{20}H_{39}N_5O_9S$ and 1,3"-N-bis-methylsulfonyl sisomicin $C_{21}H_{41}N_5O_{11}S_2$ as the TFA salts.

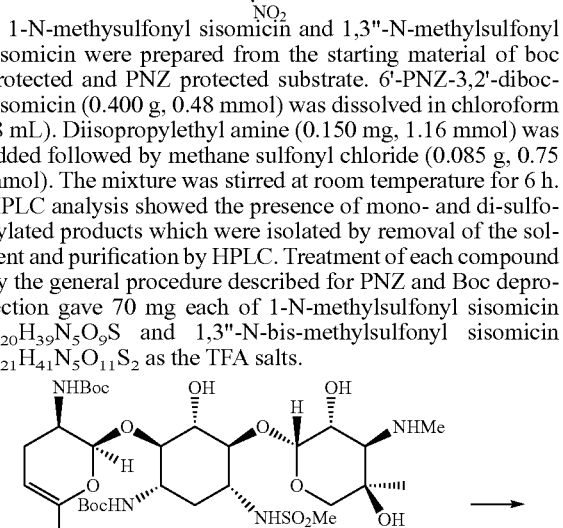

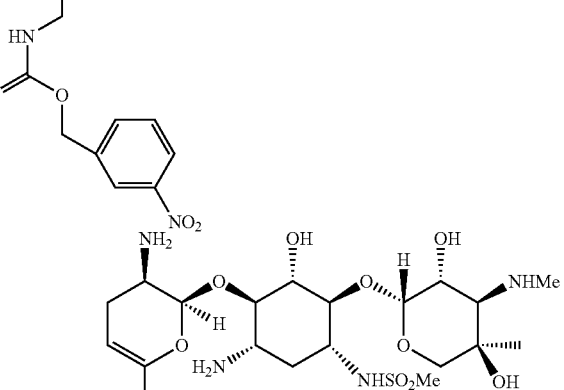

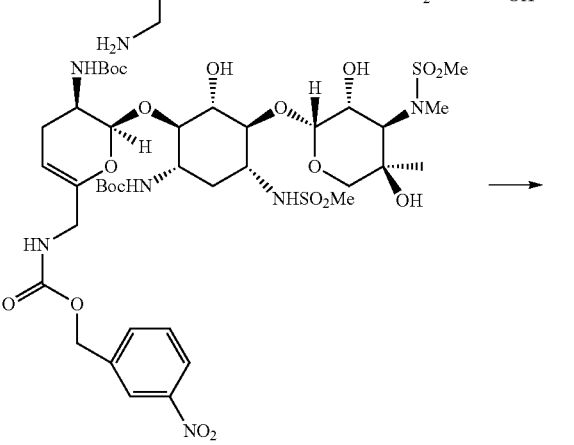

-continued

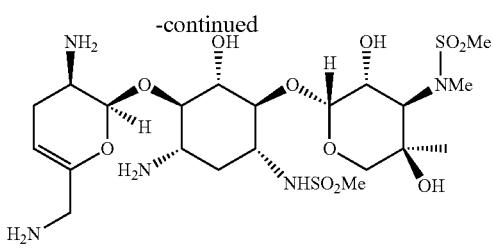

The generation of the 3"-methylsulfonyl derivative followed a similar procedure as that for 3"-benzylsulfonyl sisomicin. The diboc'd and nosylated sisomicin is the intermediate starting material.

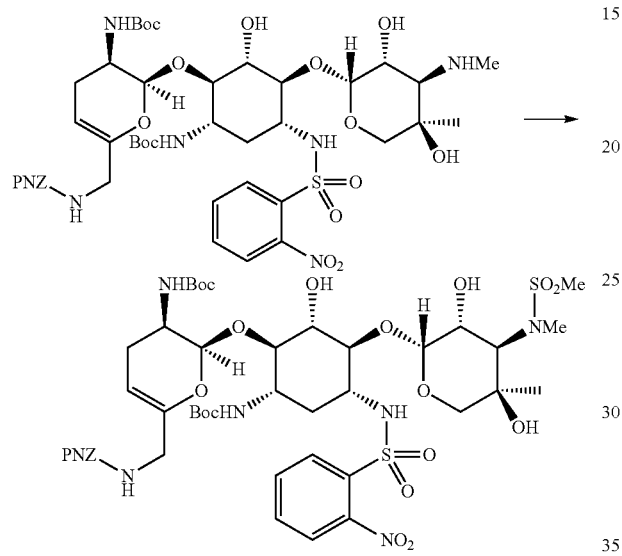

From 0.254 g 6'-PNZ-2',3-diBoc-1-Nosyl-sisomicin, following the general procedure for benzenesulfonylation procedure as described in the synthesis of 6'-PNZ-2',3-diBoc-1-Benzenesulfonyl-sisomicin, 0.126 g title compound was obtained as white solid after HPLC purification.

6'-PNZ-2',3-diBoc-3"-methylsulfonyl sisomicin

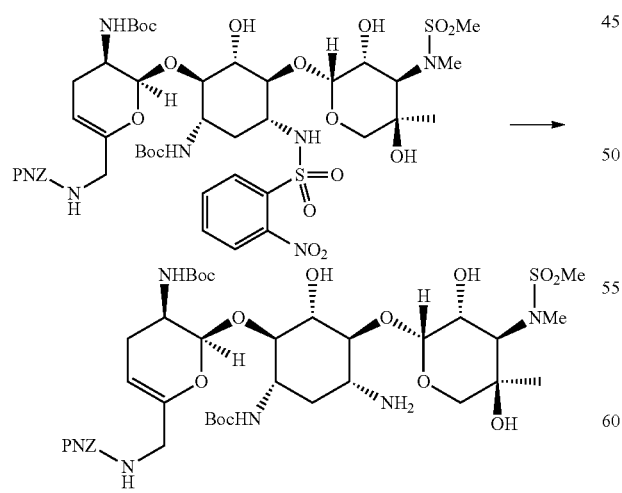

Following the general procedure for de-Nosylation, 90 mg of the title compound was obtained as white solid after HPLC purification from 0.126 g 6'-PNZ-2',3-diBoc-1-Nosyl-3"-Benzenesulfonyl sisomicin.

2',3-diBoc-3"-methylsulfonyl sisomicin

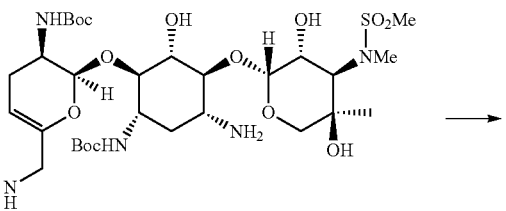

Following the general procedure for PNZ deprotection, 37 mg title compound was obtained as yellow solid after HPLC purification from 90 mg 6'-PNZ-2',3-diBoc-3"-methylsulfonyl sisomicin.

3"-methylsulfonyl sisomicin

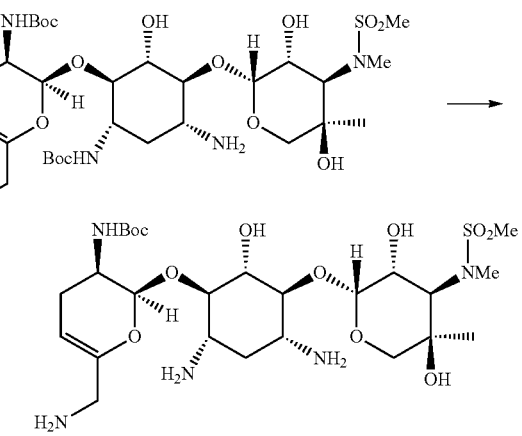

Following the general procedure for de-Boc, 39 mg title compound TFA salt was obtained as yellow solid after HPLC purification from 37 mg 2',3-diBoc-3"-methylsulfonyl sisomicin.

The Benzoyl-sisomicin derivatives were also prepared using a similar scheme for protection/deprotection. Similar to the procedure for making 3"-Benzenesulfonyl-sisomicin, benzoyl chloride instead of benzenesulfonyl chloride was used for acylation.

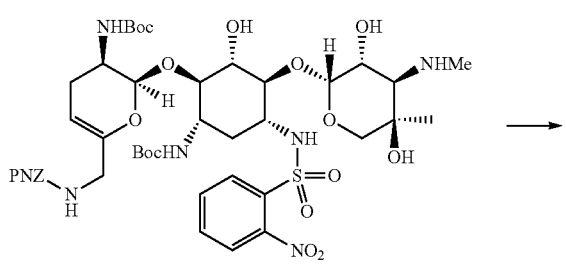

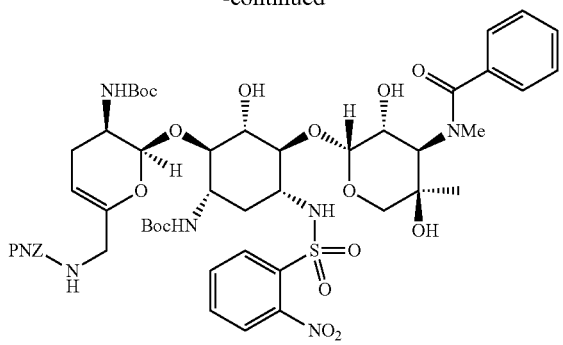

From 0.374 g 6'-PNZ-2',3-diBoc-1-Nosyl-sisomicin, following the general procedure for benzenesulfonylation procedure as described in the synthesis of 6'-PNZ-2',3-diBoc-1-Benzenesulfonyl-sisomicin, 0.295 g 6'-PNZ-2',3-diBoc-1-Nosyl-3"-Benzoyl sisomicin was obtained as yellow solid after HPLC purification.

6'-PNZ-2',3-diBoc-3"-Benzoyl sisomicin

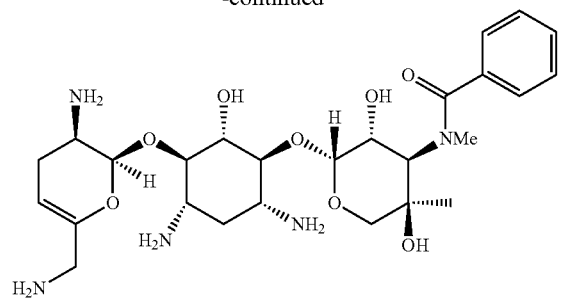

Following the general procedure for PNZ deprotection and the general procedure for de-Boc, 61 mg title compound was obtained as yellow solid after HPLC purification from 89 mg 6'-PNZ-2',3-diBoc-3"-Benzoyl sisomicin.

The 1-benzoyl sisomicin was also produced in a similar fashion starting with the double boc'ed PNZ protected substrate:

6'-PNZ-2',3-diBoc-1-benzoyl sisomicin

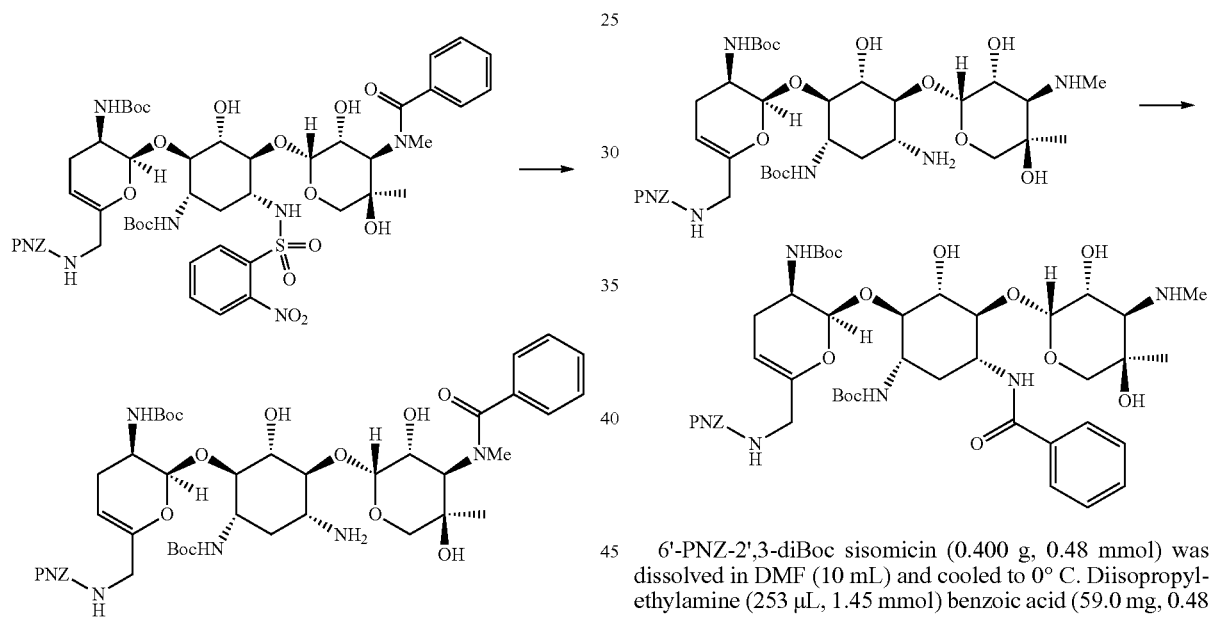

Following the general procedure for de-Nosylation, 89 mg title compound was obtained as white solid after HPLC purification from 0.295 g 6'-PNZ-2',3-diBoc-1-Nosyl-3"-Benzoyl sisomicin.

3"-Benzoyl sisomicin

6'-PNZ-2',3-diBoc sisomicin (0.400 g, 0.48 mmol) was dissolved in DMF (10 mL) and cooled to 0° C. Diisopropylethylamine (253 µL, 1.45 mmol) benzoic acid (59.0 mg, 0.48 mmol) were added followed by benzotriazole-1-yl-oxy-tris-(dimethylamino)-phosphonium hexafluorophosphate (BOP) (0.214 g, 0.48 mmol). The mixture was stirred at 0-25° C. for 1 h 15 min. After standard workup and HPLC purification, the title compound was obtained (0.438 g) (M+H=932).

2',3-diBoc-1-benzoyl sisomicin

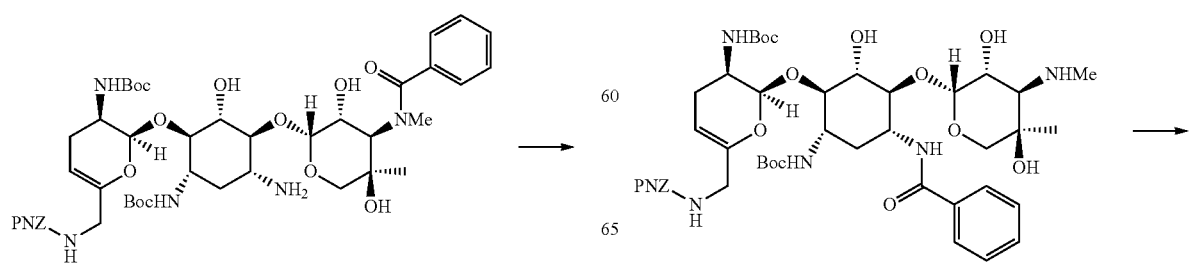

-continued

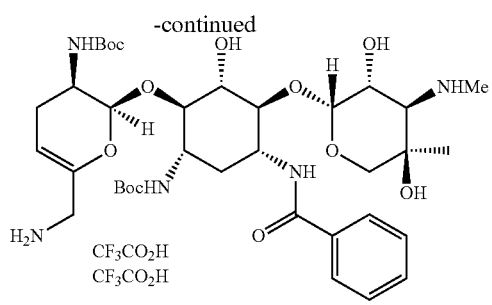

Following the standard procedure for removal of the PNZ protecting group the title compound was obtained (0.256 g, 69% yield) as the TFA salt after HPLC purification, (M+H=752).

1-benzoyl sisomicin

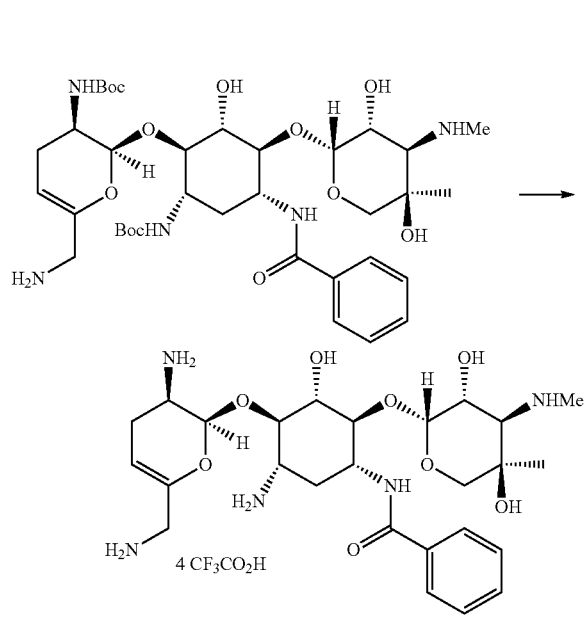

Following the standard procedure for removal of the Boc protecting groups the title compound was obtained (0.238 g, 92% yield) as the TFA salt after HPLC purification, mass spectrum (M+H=552.303).

Examples of aminoglycoside derivatives synthesized and their MS data are provided in Table 2 below.

TABLE 2

| Structure | MS (M + H) |
|---|---|
| 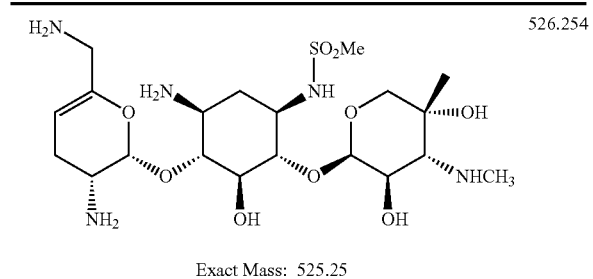<br>Exact Mass: 525.25 | 526.254 |
| 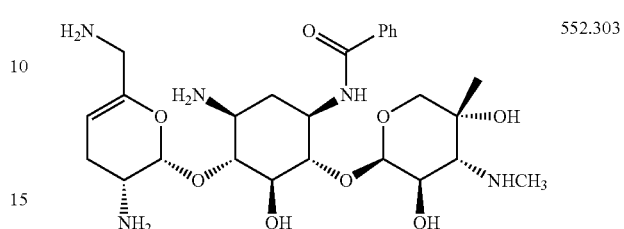<br>Exact Mass: 551.30 | 552.303 |
| 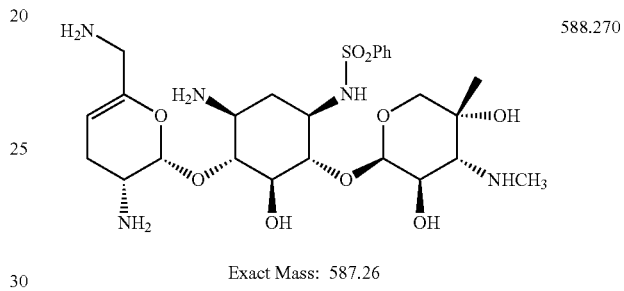<br>Exact Mass: 587.26 | 588.270 |
| 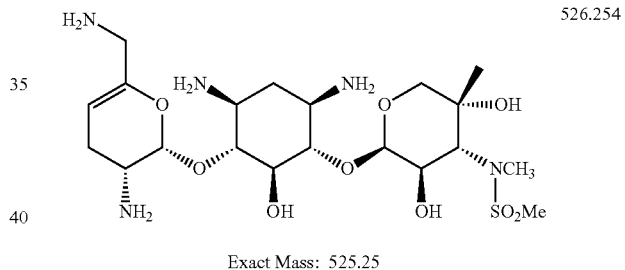<br>Exact Mass: 525.25 | 526.254 |
| 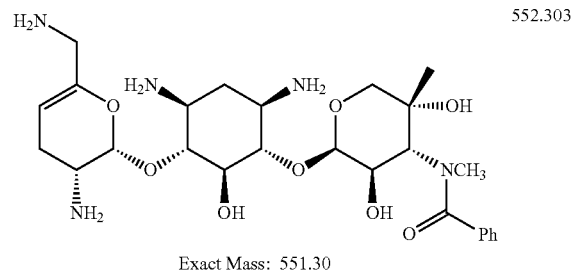<br>Exact Mass: 551.30 | 552.303 |
| 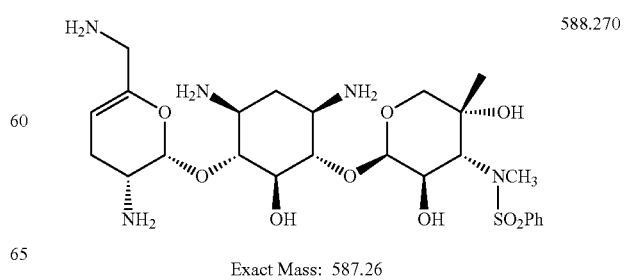<br>Exact Mass: 587.26 | 588.270 |

TABLE 2-continued

| Structure | MS (M + H) |
|---|---|
| [Structure with Exact Mass: 603.22, H₂N, SO₂Me, NH, OH, NH₂, OH, OH, NCH₃, SO₂Me] | 604.232 |
| [Structure with Exact Mass: 655.32, H₂N, COPh, NH, OH, NH₂, OH, OH, NCH₃, COPh] | 656.329 |
| [Structure with Exact Mass: 727.26, H₂N, SO₂Ph, NH, OH, NH₂, OH, OH, NCH₃, SO₂Ph] | 728.263 |

Example 7

Conversion of TFA Salt of Aminoglycosides to Sulfate Salt

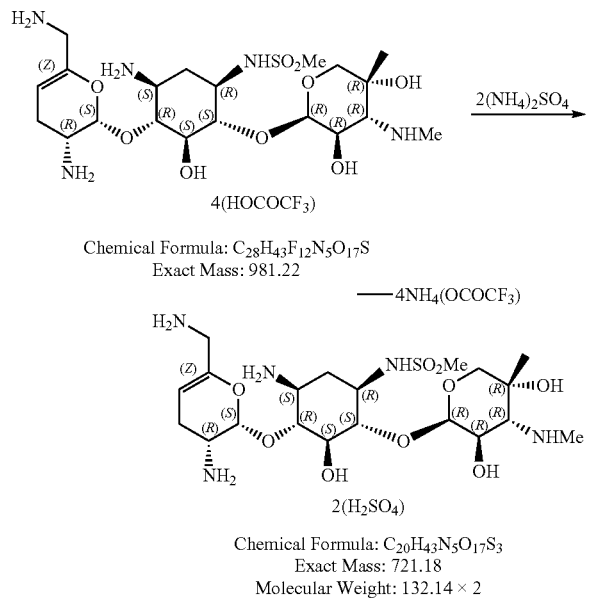

Chemical Formula: $C_{28}H_{43}F_{12}N_5O_{17}S$
Exact Mass: 981.22

Chemical Formula: $C_{20}H_{43}N_5O_{17}S_3$
Exact Mass: 721.18
Molecular Weight: 132.14 × 2

The TFA salt as shown in the scheme above (17.66 mg, 0.018 mmol) was dissolved in Water (0.1 mL). The pH was about 5. NH₄OH (10 μl) was added to raise the pH to about 7. Ammonium sulfate (4.76 mg, 0.036 mmol) was added and then the solution was added dropwise to vigorously stirred methanol (2.000 mL, which was a sufficient amount of methanol used as the anti-solvent to precipitate the desired product.) The resulting solid was isolated in portions (e.g., 1 mL resulting mixture to a centrifuge tube at a time) by centrifugation, and rinsed with methanol (2×0.5 mL).

Example 8

Biological Activity

Both antimicrobial activity and ototoxicity in several of the synthesized compounds were assessed. To test antimicrobial activity, an *E. coli* assay was used to test both minimal inhibitory concentrations (MIC) as well as minimal bactericidal concentrations (MBC). A cross section of results was presented in FIG. 1, for control and a variety of tested compounds. As shown in FIGS. 1A and 1B, antimicrobial activity was maintained but it depends specifically on the nature of the substituent. Antimicrobial activity remained stable for each compound over time.

Figure 2:
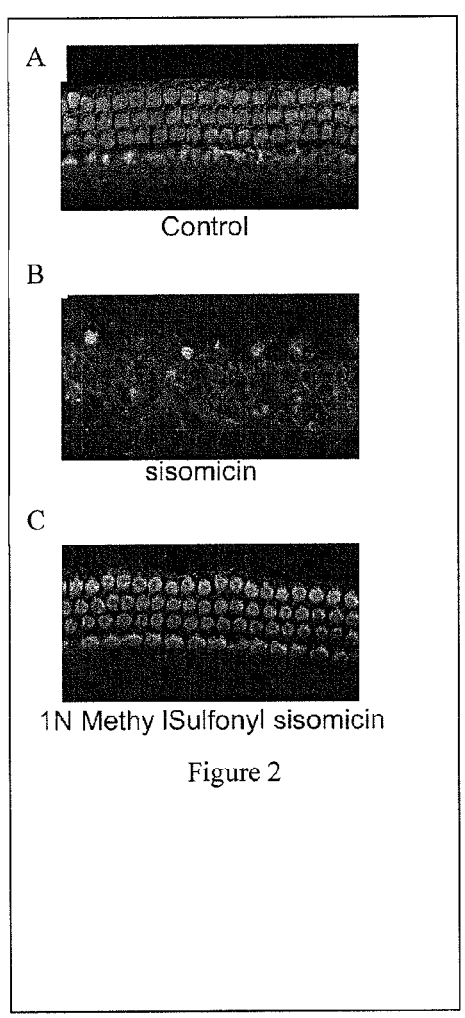
FIGS. 2A-2C are a series of images showing Myosin VII stained organotypical cochlear cultures showing control (A) or samples following treatment with sisomicin (B), or sisomicin substituted with methyl sulfonyl at the 1N position ("1N-MS sisomicin") (C).
Figure 3:
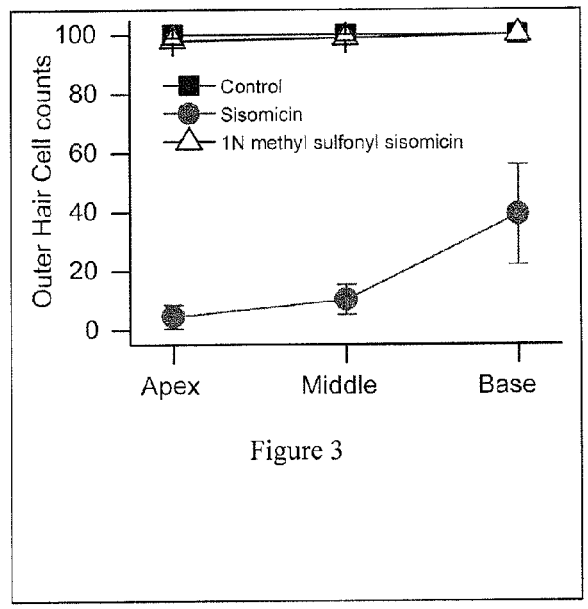
FIG. 3 is a summary plot of hair cell counts following treatment with either sisomicin or 1N-MS sisomicin.
Figure 4:
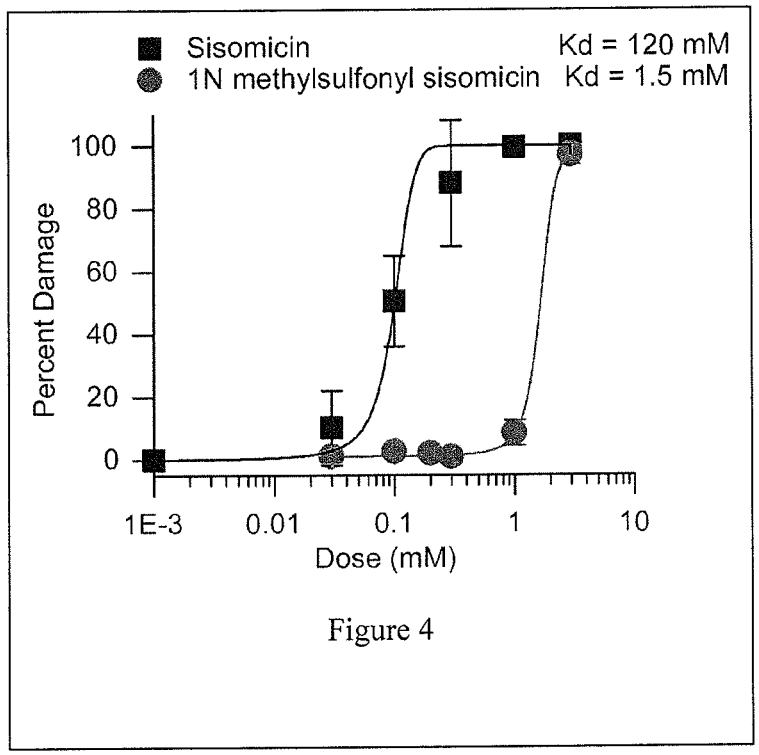
FIG. 4 is a dose response curve for the parent sisomicin and 1N-MS sisomicin from the organ tissue culture preparation. 1N-MS sisomicin shows a more than ten-fold shift in sensitivity for toxicity.

Ototoxicity was also assayed using cochlea organ of corti cultures. The cultures were made at 4 days post birth (P4), cultured for 1 day and then treated for 1 hour with test compound. The tissue was then washed and cultured for an additional two days at which time the tissue is fixed and stained so that hair cell counts could be obtained. This method is similar to that used previously in characterizing aminoglycoside ototoxicity (Alharazneh et al., 2011). Fixed regions at the apex, middle, and base of the cochlea were imaged and cell counts obtained. FIG. 2 shows example of parvalbumin labeled hair cells from control (A), parent aminoglycoside (B) or tested novel aminoglycoside (C) treated tissue. FIG. 2A (with controls) shows that all hair cells were intact. FIG. 2B demonstrates that the tissue, following two days after a 1 hr incubation with sisomicin, had no hair cells remained. FIG. 2C shows that the tissue, with a similar treatment paradigm with 1N-methyl sulfonyl sisomicin, had no hair cell loss. Data were quantified across cochlear regions for this same compound. Quantification was by counting the number of outer hair cells present over a given distance. A summary of these data is presented in FIG. 3. At the same concentration the parent compound kills more than 90% of outer hair cells in the base and middle and about 60% of the cells at the apex. The test compound (i.e., 1N-methyl sulfonyl sisomicin) did not cause any hair cell loss at any of the cochlea regions tested. A dose response curve was created for the parent compound as well as the tested novel aminoglycoside. This is presented in FIG. 4. Here plots of compound concentration against percent damage again illustrate the lack of toxicity of the novel aminoglycoside. The data were fit with Hill Equation and Kds of 120 μM and 1.5 mM obtained for parent sisomicin and 1N-methyl sulfonyl sisomicin, respectively. In other words, 1N-methyl sulfonyl sisomicin is more than 10× less toxic than the parent compound. This particular compound also retained antimicrobial activity. Other sisomicin derivatives were also tested for ototoxicity. 3"N-methyl sulfonyl sisomicin and 1N,3"N-methyl sulfonyl sisomicin were about equally non-ototoxic as 1N-methyl sulfonyl sisomicin. 1N phenyl sulfonyl sisomicin was about 80% less toxic than sisomicin. 3"N- and 1N,3"N-phenyl sulfonyl derivatives were about equally ototoxic as sisomicin. 1N benzoyl sisomicin was 30% less toxic and 3"N-benzoyl sisomicin was about 60% less toxic than the parent compound. The rhodamine tagged sisomicin was equally as toxic as the parent compound.

Figure 5:
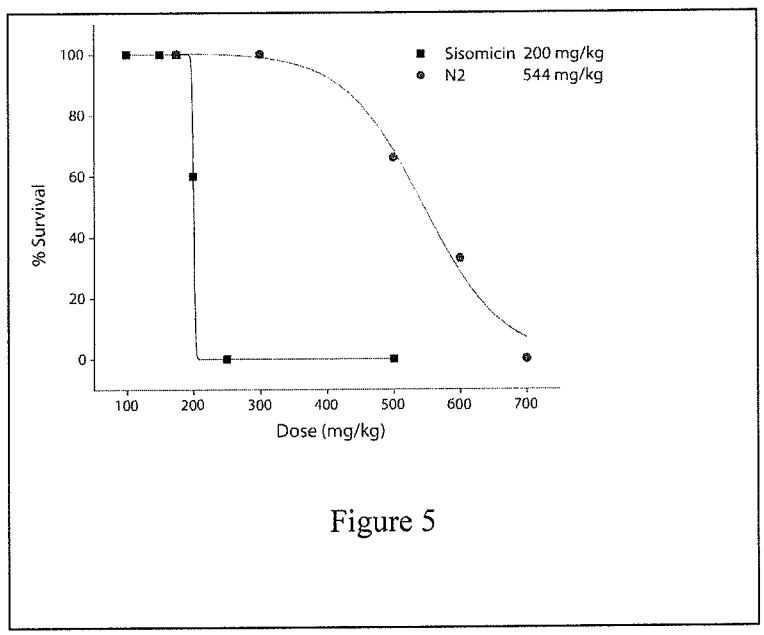
FIG. 5 is a plot of $LD_{50}$ values demonstrating lethal doses for sisomicin and 1N-MS sisomicin (labeled as N2 in this figure) in an animal model.
Figure 6:
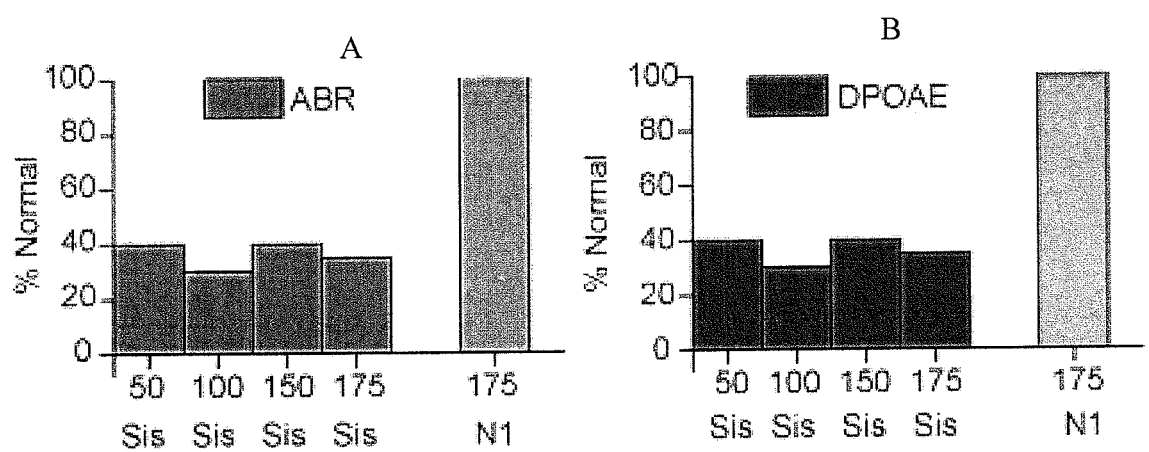
FIGS. 6A and 6B are bar graphs demonstrating auditory brainstem response (ABR) (A) and distortion product otoacoustic emission (DPOAEs) (B) in an animal model treated with sisomicin or 1N-MS sisomicin (labeled as N1 in this figure) in combination with furosemide.

Ototoxicity of the aminoglycosides derivatives was also tested on animals. A mouse model was developed for hearing loss using sisomicin as the parent compound, combined with furosemide as co-treatment. Prior to hearing loss development, an $LD_{50}$ value was obtained by injecting intraperitoneally with either sisomicin or the 1N-methyl sulfonyl derivative. As shown in FIG. 5, the $LD_{50}$ of 1N-methyl sulfonyl sisomicin is 3× higher than $LD_{50}$ of the parent sisomicin. Auditory brainstem responses (ABR) as well as distortion product otoacoustic emissions (DPOAEs) were measured prior to drug treatments and 1 week following a single high dose administered intraperitoneally concomitantly with a single dose of furosemide. Results presented in FIGS. 6A and 6B show that at comparable high doses, 175 mg/kg, sisomicin treatment resulted in more than 60% hearing loss measured by both parameters, while the treatment with 1N-methyl sulfonyl sisomicin (labeled as N1 in this figure) showed no measurable hearing loss. Histological preparations of the cochlea following measurements similarly showed no loss of hair cells with 1N-methyl sulfonyl sisomicin treatment as compared to significant hair cell loss using the parent sisomicin compound.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

The invention claimed is:
1. A compound of Formula (I) or a pharmaceutically acceptable salt thereof:

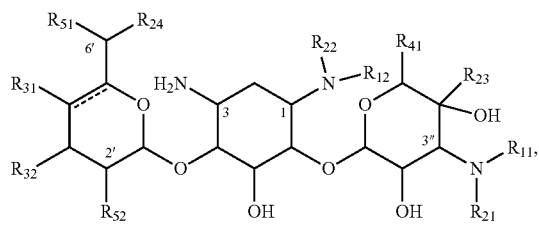

(I)

wherein
the ═══ bond is a single bond or double bond;
each of $R_{11}$ and $R_{12}$ independently is H, $C(O)R_a$, $C(O)OR_a$, $C(O)NHR_a$, $C(O)NR_aR_b$, or $S(O)_nR_a$, in which n is 1, or 2, and each of $R_a$ and $R_b$, independently is $C_1$-$C_{20}$ alkyl, $C_2$-$C_{20}$ alkenyl, $C_2$-$C_{20}$ alkynyl, $C_3$-$C_8$ cycloalkyl, $C_6$-$C_{10}$ aryl, 4 to 12-membered heterocycloalkyl, or 5 to 14-membered heteroaryl; or $R_a$ and $R_b$, together with the N atom to which they are attached, form a 4 to 12-membered heterocycloalkyl ring having 0 or 1 additional heteroatom; and each of $R_a$, $R_b$, and the 4 to 12-membered heterocycloalkyl ring formed by $R_a$ and $R_b$, is optionally substituted;

each of $R_{21}$, $R_{22}$, $R_{23}$, and $R_{24}$, independently, is H or optionally substituted $C_1$-$C_6$ alkyl;
each of $R_{31}$ and $R_{32}$, independently, is H or OH;
$R_{41}$ is H or $CH_2OH$; and
each of $R_{51}$ and $R_{52}$, independently, is OH, $NH_2$, unsubstituted mono-$C_1$-$C_6$ alkylamino, or unsubstituted di-$C_1$-$C_6$ alkylamino,
provided that at least one of $R_{11}$ and $R_{12}$ is not H; further when $R_{12}$ is $C(O)R_a$ or $S(O)_2R_a$, then (i) $R_a$ is not alkyl substituted with $NH_2$ or (ii) $R_a$ is unsubstituted alkyl or alkyl substituted with one or more -Q-T, wherein Q is a bond or $C_1$-$C_3$ alkyl linker each optionally substituted with halo, cyano, hydroxyl or $C_1$-$C_6$ alkoxy, and T is H, halo, cyano, —$OR_c$, —$C(O)R_c$, —$C(O)OR_c$, —$C(O)NR_cR_d$, —$NR_dC(O)R_c$, —$NR_dC(O)OR_c$, —$S(O)_2R_c$, —$S(O)_2NR_cR_d$, $R_{S1}$, —$NHR_{S1}$, or —$N(R_{S1})_2$, in which each of $R_c$ and $R_d$, independently is H or $R_{S2}$, each of $R_{S1}$ and $R_{S2}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl; or $R_c$ and $R_d$, together with the N atom to which they are attached, form a 4 to 12-membered heterocycloalkyl ring having 0 or 1 additional heteroatom or 5 to 14-membered heteroaryl.

2. The compound of claim 1, wherein $R_{11}$ is H and $R_{12}$ is not H.
3. The compound of claim 2, wherein $R_{12}$ is $C(O)R_a$ or $S(O)_2R_a$.
4. The compound of claim 1, wherein $R_{12}$ is H and $R_{11}$ is not H.
5. The compound of claim 4, wherein $R_{11}$ is $C(O)R_a$ or $S(O)_2R_a$.
6. The compound of claim 1, wherein neither of $R_{11}$ and $R_{12}$ is H.
7. The compound of claim 6, wherein each of $R_{11}$ and $R_{12}$ independently is $C(O)R_a$ or $S(O)_2R_a$.
8. The compound of claim 1, wherein each of $R_a$ and $R_b$, independently is $C_1$-$C_{20}$ alkyl, $C_2$-$C_{20}$ alkenyl, $C_2$-$C_{20}$ alkynyl, $C_3$-$C_8$ cycloalkyl, $C_6$-$C_{10}$ aryl, 4 to 12-membered heterocycloalkyl, or 5 to 14-membered heteroaryl, each optionally substituted with one or more
-Q-T, wherein Q is a bond or $C_1$-$C_3$ alkyl linker each optionally substituted with halo, cyano, hydroxyl or $C_1$-$C_6$ alkoxy, and T is H, halo, cyano, —$OR_c$, —$NR_cR_d$, —$C(O)R_c$, —$C(O)OR_c$, —$C(O)NR_cR_d$, —$NR_dC(O)R_c$, —$NR_dC(O)OR_c$, —$S(O)_2R_c$, —$S(O)_2NR_cR_d$, or $R_{S1}$, in which each of $R_c$ and $R_d$, independently is H or $R_{S2}$, each of $R_{S1}$ and $R_{S2}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl; or $R_c$ and $R_d$, together with the N atom to which they are attached, form a 4 to 12-membered heterocycloalkyl ring having 0 or 1 additional heteroatom.

9. The compound of claim 8, wherein each of $R_a$ independently is methyl or ethyl each of which is optionally substituted by one or more halo or $C_3$-$C_8$ cycloalkyl, optionally substituted $C_3$-$C_{10}$ alkyl, optionally substituted $C_3$-$C_8$ cycloalkyl, optionally substituted $C_3$-$C_{10}$ alkenyl, optionally substituted $C_3$-$C_{10}$ alkynyl, optionally substituted $C_6$-$C_{10}$ aryl, or optionally substituted 5 to 10-membered heteroaryl.

10. The compound of claim 1, each of $R_{21}$, $R_{22}$, $R_{23}$, and $R_{24}$, independently, is H or $C_1$-$C_6$ alkyl optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

11. The compound of claim 10, wherein each of $R_{21}$, $R_{22}$, $R_{23}$, and $R_{24}$, independently, is H or unsubstituted $C_1$-$C_6$ alkyl.

12. The compound claim 1, wherein the compound is of Formula (II) or a pharmaceutically acceptable salt thereof:

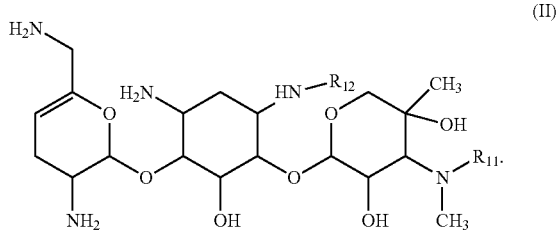

(II)

13. The compound of claim 12, wherein the compound is of any of Formula (IIA), (IIB), or (IIC), or a pharmaceutically acceptable salt thereof:

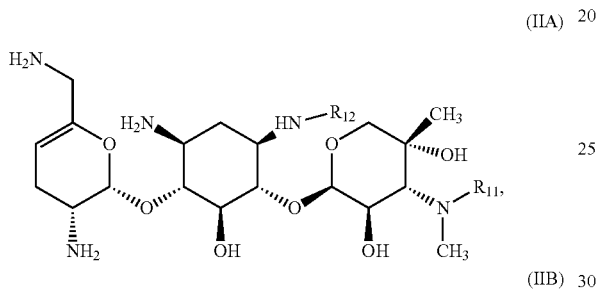

(IIA)

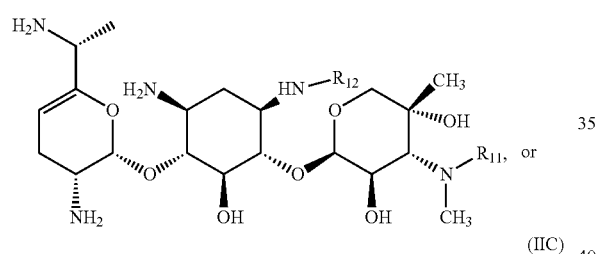

(IIB)

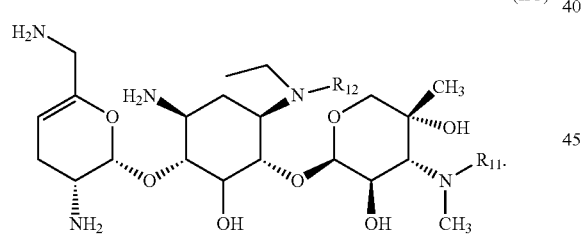

(IIC)

14. A compound of Formula (III) or a pharmaceutically acceptable salt thereof:

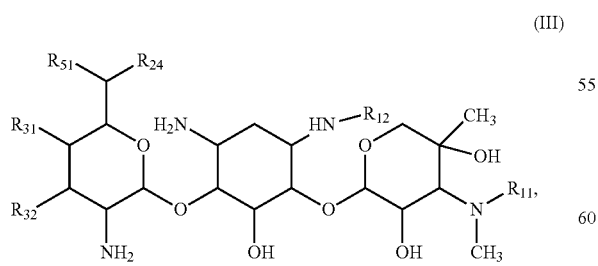

(III)

wherein
each of $R_{11}$ and $R_{12}$ independently is H, $C(O)R_a$, $C(O)OR_a$, $C(O)NHR_a$, $C(O)NR_aR_b$, or $S(O)_nR_a$, in which n is 1, or 2, and each of $R_a$ and $R_b$, independently is $C_1$-$C_{20}$ alkyl, $C_2$-$C_{20}$ alkenyl, $C_2$-$C_{20}$ alkynyl, $C_3$-$C_8$ cycloalkyl, $C_6$-$C_{10}$ aryl, 4 to 12-membered heterocycloalkyl, or 5 to 14-membered heteroaryl; or $R_a$ and $R_b$, together with the N atom to which they are attached, form a 4 to 12-membered heterocycloalkyl ring having 0 or 1 additional heteroatom; and each of $R_a$, $R_b$, and the 4 to 12-membered heterocycloalkyl ring formed by $R_a$ and $R_b$, is optionally substituted; provided that at least one of $R_{11}$ and $R_{12}$ is not H;

$R_{24}$ is H or methyl;

$R_{31}$ and $R_{32}$ are the same and are H or OH; and $R_{51}$ is OH, $NH_2$, or $NHCH_3$.

15. The compound of claim 14, wherein the compound is of any of Formulae (IIIA)-(IIIF) or a pharmaceutically acceptable salt thereof:

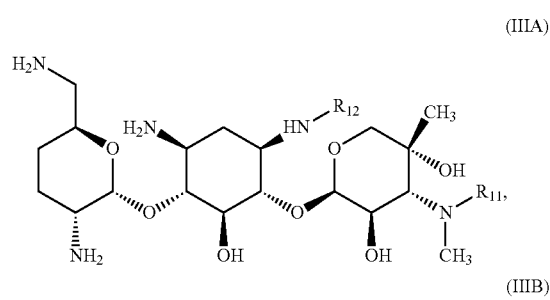

(IIIA)

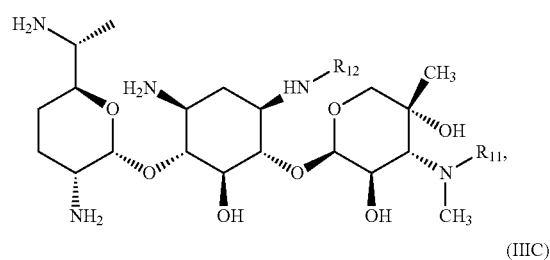

(IIIB)

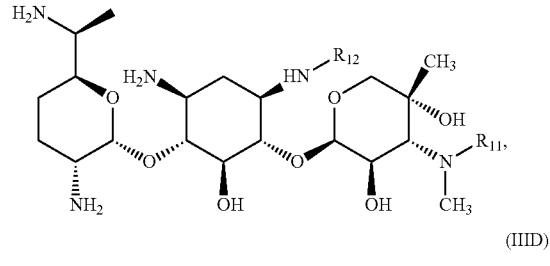

(IIIC)

(IIID)

(IIIE)

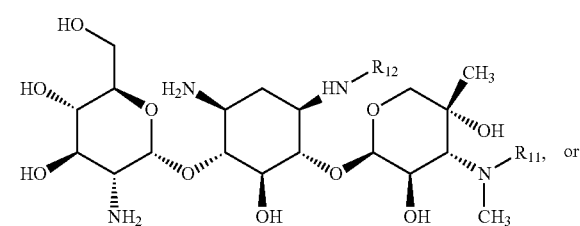

, or (IIIF)

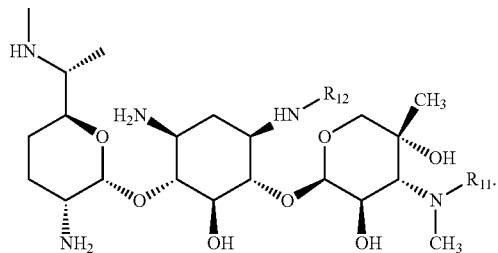

16. The compound of claim 1, wherein the compound is of Formula (IV) or a pharmaceutically acceptable salt thereof:

(IV)

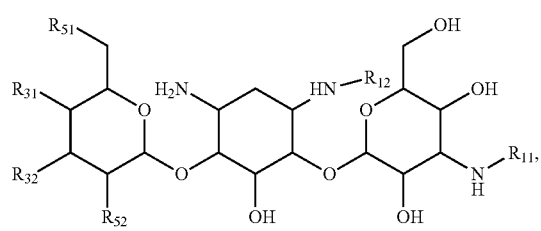

wherein each of $R_{51}$ and $R_{52}$, independently, is OH or $NH_2$.

17. The compound of claim 16, wherein the compound is of any of Formulae (IVA)-(IVE) or a pharmaceutically acceptable salt thereof:

(IVA)

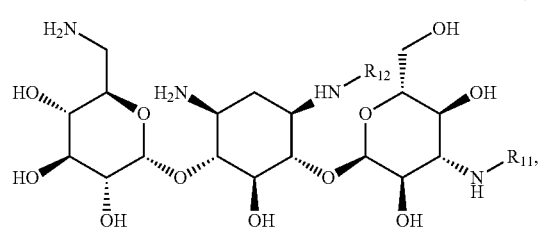

(IVB)

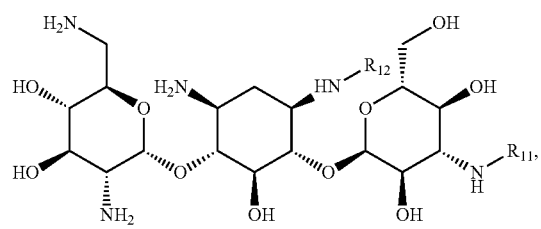

(IVC)

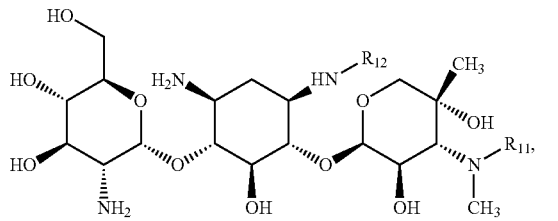

(IVD)

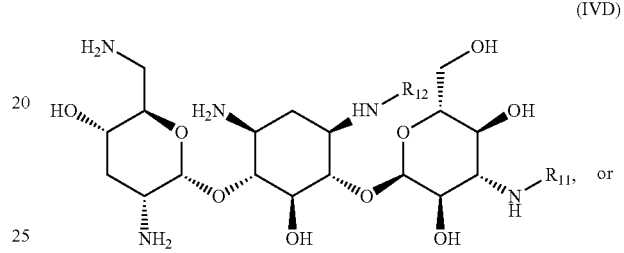

(IVE)

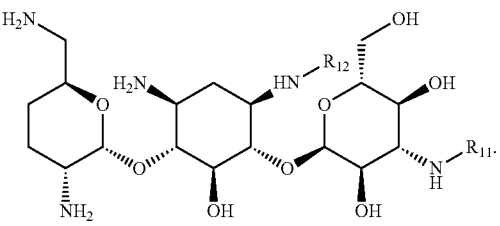

18. A pharmaceutical composition comprising a compound of claim 1 or a pharmaceutically acceptable salt thereof and a pharmaceutically acceptable carrier.

19. A method of treating a bacterial infection comprising administering to a subject in need thereof a therapeutically effective amount of a compound of claim 1 or a pharmaceutically acceptable salt thereof.

* * * * *